US007667097B2

(12) United States Patent
Scheirlinck et al.

(10) Patent No.: US 7,667,097 B2
(45) Date of Patent: Feb. 23, 2010

(54) RICE POLLEN-PREFERENTIAL PROMOTERS AND USES THEREOF

(75) Inventors: Marie-Therese Scheirlinck, Zottegem (BE); Eva Perez-Prat Vinuesa, Newcastle upon Tyne (GB); Jean Broadhvest, Lovendegem (BE)

(73) Assignee: Bayer Bioscience N.V., Ghent (BE)

( * ) Notice: Subject to any disclaimer, the term of this patent is extended or adjusted under 35 U.S.C. 154(b) by 35 days.

(21) Appl. No.: 11/578,428

(22) PCT Filed: Apr. 13, 2005

(86) PCT No.: PCT/EP2005/004009

§ 371 (c)(1),
(2), (4) Date: Oct. 13, 2005

(87) PCT Pub. No.: WO2005/100575

PCT Pub. Date: Oct. 27, 2005

(65) Prior Publication Data
US 2008/0034451 A1 Feb. 7, 2008

Related U.S. Application Data

(60) Provisional application No. 60/561,878, filed on Apr. 14, 2004.

(51) Int. Cl.
*C12N 15/82* (2006.01)
*A01H 5/00* (2006.01)
*C12N 5/04* (2006.01)
*C07H 21/04* (2006.01)

(52) U.S. Cl. .................. 800/287; 800/285; 800/286; 800/288; 800/295; 800/298; 435/419; 435/468; 435/320.1; 536/23.1; 536/24.1; 536/24.5

(58) Field of Classification Search .................. None
See application file for complete search history.

(56) References Cited

U.S. PATENT DOCUMENTS

| 5,641,664 | A | 6/1997 | D'Halluin et al. |
| 5,679,558 | A | 10/1997 | Gobel et al. |
| 5,712,126 | A | 1/1998 | Weissman et al. |
| 5,744,336 | A | 4/1998 | Hodges et al. |
| 2004/0016025 | A1 | 1/2004 | Budworth et al. |
| 2007/0039076 | A1* | 2/2007 | Boukharov et al. ...... 800/320.2 |

FOREIGN PATENT DOCUMENTS

| WO | WO 89/10396 | 11/1989 |
| WO | WO 93/19188 | 9/1993 |
| WO | WO 93/25695 | 12/1993 |
| WO | WO 96/26283 | 8/1996 |
| WO | WO 97/30166 | 8/1997 |
| WO | WO 98/10081 | 3/1998 |
| WO | WO 99/05281 | 2/1999 |
| WO | WO 99/42587 | 8/1999 |
| WO | WO 99/53050 | 10/1999 |
| WO | WO 03/031613 | 4/2003 |

OTHER PUBLICATIONS

Eyal et al. Pollen specificity elements reside in 30 bp of the proximal promoters of two pollen-expressed genes. (1995) The Plant Cell; vol. 7, pp. 373-384.*
Kyozuka et al. Promoter elements required for developmental expression of the maize Adh1 gene in transgenic rice. (1994) The Plant Cell; vol. 6, pp. 799-810.*
Tsuchiya et al. Molecular characterization of rice genes specifically expressed in the anther tapetum. (1994) PMB; vol. 26, pp. 1737-1746.*
Eyal et al. Pollen specificity elements reside in 30 bp of the proximal promoters of two pollen-expressed genes. (1995) The Plant Cell; vol. 7, pp. 373-384.*
Benfey et al. The Cauliflower Mosaic Virus 35S promoter: combinatorial regulation of transcription in plants. (1990) Science; vol. 250, pp. 959-966.*
Kim et al. A 20 nucleotide upstream element is essential for the nopaline synthase (nos) promoter activity. (1994) PMB; vol. 24, pp. 105-117.*
Hsing et al. GenBank Accession AC093952; published on Mar. 29, 2003; pp. 1-38.*
Diego Albani, et al., "A *Brassics napus* gene family which shows sequence similarity to ascorbate oxidase is expressed in developing pollen. Molecular characterization and analysis of promoter activity in transgenic Tobacco Plants", The Plant Journal, vol. 2, No. 3, p. 331-342, 1992.
Yoram Eyal, et al., "Pollen Specificty Elements Reside in 30 bp of the Proximal Promoters of Two-Pollen Expressed Genes", The Plant Cell, vol. 7, p. 373-384, Mar. 1995.
Doris D. Hanson, et al., "Characterization of a Pollen-Specific cDNA Clone from *Zea mays* and its Expression", The Plant Cell, vol. 1, p. 173-179, Feb. 1989.
D. A. Hamilton, et al., "Characterization of a Pollen-Specific Genomic Clone from Maize", Sex Plant Reprod., vol. 2, p. 208-212, 1989.
Douglas A. Hamilton, et al., "Dissection of a Pollen-Specific Promoter from Maize by transient transformaton Assays", Plant Molecular Biology, vol. 18, p. 211-218, 1992.
Raymond J. M. Hulzink, et al., "The 5'-Untranslated Region of the *ntp303* Gene Strongly Enhances Translation during Pollen Tube Growth, But Not during Pollen Maturation", Plant Physiology, vol. 129, p. 342-353, May 2002.
Sheila McCormick, et al., "Molecular Analysis of Gene Regulation and Function During Male Gametophyte Development", Symp. Soc. Exp. Biol., vol. 45, p. 229-244, 1991.

(Continued)

*Primary Examiner*—Cathy Kingdon Worley
(74) *Attorney, Agent, or Firm*—Hunton & Williams LLP

(57) ABSTRACT

The present invention relates to rice genomic promoter sequences which promote transcription preferentially in microspores and/or pollen of plants. Also provided are chimeric genes comprising these promoter sequences, and plant transformation vectors comprising these chimeric genes. The present invention also discloses plant cells, plant tissues, plants, seeds and grains comprising these chimeric genes. The invention further discloses methods for expressing foreign nucleic acid sequences preferentially in pollen and for producing plants with modified pollen fertility.

24 Claims, 1 Drawing Sheet

OTHER PUBLICATIONS

Manjit Singh, et al., "Isolation and Characterization of a Flowering Plant Male Gametic Cell-Specific promoter", FEBS Letters, vol. 542, p. 47-52, 2003.

David Twell, et al., "Promoter Analysis of Genes that are coordinately expressed during Pollen development reveals Pollen-Specific enhancer sequences and shared Regulatory Elements", Genes & Development, vol. 5, p. 496-507, 1991.

Koen Weterings, et al., "Characterization of a Polllen-Specfic cDNA clone from *Nicotiana tabacum* expressed during Microgametogenesis and Germination", Plant Molecular Biology, vol. 18, p. 1101-1111, 1992.

Koen Weterings, et al., "Functional Dissection of the Promoter of the Pollen-Specific gene *NTP303* reveals a novel Pollen-Specific, and conserved *cis*-regulated element", The Plant Journal, vol. 8, No. 1, p. 55-63, 1995.

Huiling Xu, et al., "Male Gametic Cell-Specific Gene Expression in Flowering Plants", Proc. Natl. Acad Sci, vol. 96, p. 2554-2558, Mar. 1999.

Xiao-yan Zhan, et al., "Nuclear Male Sterility induced by Pollen-Specific Expression of a ribonuclease", Sex Plant Reprod., vol. 9, p. 35-43, 1996.

Ji-Tao Zou, et al., "Characterization of a Rice Pollen-Specific Gene and its Expression", American Journal of Botany, vol. 81, No. 5, p. 552-561, 1994.

Chow and Hsing, Database EMBL, accession No. AC093952, Sep. 17, 2001.

Weterings, Database EMBL, accession No. X61146 (referencing Swiss-Prot accession No. P29162), Jun. 29, 1992.

Wing, Database EMBL, accession No. AQ577962, Jun. 3, 1999.

Michalowski, Database EMBL, accession No. BE041021, Jun. 14, 2000.

Sasaki, Database EMBL, accession No. C72996, Sep. 19, 1997.

Adachi et al., Database EMBL, accession No. AK108702, Jul. 19, 2003.

Sasaki, Database EMBL, accession No. AU101215, Aug. 17, 2000.

Sasaki, Database EMBL, accession No. AU093980, Jun. 29, 2000.

Sasaki, Database EMBL, accession No. C72986, Sep. 19, 1997.

Sasaki, Database EMBL, accession No. AU172461, Jan. 30, 2001.

Yu et al., Database EMBL, accession No. AAAA01001318, May 9, 2002.

\* cited by examiner

SEQUENCE LISTING

<160> NUMBER OF SEQ ID NOS: 10

<210> SEQ ID NO 1
<211> LENGTH: 29
<212> TYPE: DNA
<213> ORGANISM: Artificial
<220> FEATURE:
<223> OTHER INFORMATION: oligonucleotide primer TSOL22

```
<400> SEQUENCE: 1
cggggtaccg ggaagacgta cagattgcg                                29

<210> SEQ ID NO 2
<211> LENGTH: 31
<212> TYPE: DNA
<213> ORGANISM: Artificial
<220> FEATURE:
<223> OTHER INFORMATION: oligonucleotide primer TSOL23

<400> SEQUENCE: 2
gacccaagct tgcggttggc cgtgaacagc a                             31

<210> SEQ ID NO 3
<211> LENGTH: 180
<212> TYPE: DNA
<213> ORGANISM: Oryza sativa

<400> SEQUENCE: 3
gggaagacgt acagattgcg cgtctccaac gtcggcctgc agagcacgct caatttgagg    60
atccaagacc acaacatgac gctggtcgag gtggagggca cgcacacggt gcagaacaac   120
tacagctccc tctacgtcca cgccggccag tcgctgtccg tgctgttcac ggccaaccgc   180

<210> SEQ ID NO 4
<211> LENGTH: 4000
<212> TYPE: DNA
<213> ORGANISM: Oryza sativa
<220> FEATURE:
<221> NAME/KEY: promoter region
<222> LOCATION: (320)..(1431)
<220> FEATURE:
<221> NAME/KEY: transcription start site
<222> LOCATION: (1236)..(1236)
<220> FEATURE:
<221> NAME/KEY: transcription start site
<222> LOCATION: (1244)..(1244)
<220> FEATURE:
<221> NAME/KEY: translation initiation codon
<222> LOCATION: (1432)..(1434)
<220> FEATURE:
<221> NAME/KEY: Intron
<222> LOCATION: (2798)..(3361)
<220> FEATURE:
<221> NAME/KEY: polyA_site
<222> LOCATION: (3946)..(3946)
<220> FEATURE:
<221> NAME/KEY: polyA_site
<222> LOCATION: (3949)..(3949)

<400> SEQUENCE: 4
aaggagttgt atcataaaac tacacattta gcatcaaatt tatcacaaaa ctgcagattt    60
taggttaagt atcacaaaaa tacatattta atattgaact tatcacaaaa ctataacttt   120
tggagtttaa atccctagca ccattgttat ggtggagcta taaacattat tactttgtga   180
ttaaattggt tctaaacctt tagttttatg ataatttagt aactaaacgt gtagttttgt   240
aacacttcat ctttaatatg tagttttgtg ctaaatttgg tgctaaatgt gtaattttgt   300
gatataattc cttaaatatg tagttttgtg atagtttggt tataatatct gtagttttat   360
gaaatttact cttttcgttt tcactgcaat ttggaatgat ggaattgact agatccggca   420
ttaccgatgg gctgccgaac gctgtgatgc ggttgatctt gagcgatccg ggacgccaca   480
agcaccgatg ggttctggga gttcatacgc ctggtgcagc agtgtgtcaa tagcagccgg   540
gatgtgcgcc caaccatggt cgccgtcgag aggaggatcg aagacatcct gaactcggtt   600
```

-continued

```
gtcaggtcat ccaccaccgg gttcatgact gccggaggcg acacacccag caacgagcca      660
aatcgtgaag ataacggaaa cgagccaaat cccagcaacg agatcgccag ggactagtag      720
tacgtacagc agtggtgatt tgtcatatag gtgtatatcg gctgttttcg catctcaagg      780
cctcaagcag tgtgtgcaat ctggagtagt atataaatat gtaaaatgtt catttcgata      840
tactgtcaaa tgcgtgtaaa ttaaccaatg ctaaaacaac acactgtgac taaatttact      900
gagttggatg atgaggatga ttatgttgcg tgcacacctg atcaggagga catataatat      960
aggccatttg ggccgtcttg gacaccaccg tttgatttgt atgaagttgg gccgaactat     1020
gcaagcccag aggcgctgcc tctgtgccac ggcccacggg catcgctgga tggtcaagca     1080
ggtgatcggt ggagcgccaa tggcggcggc gagacacaca gcgcggcgcg cgcgcgaacg     1140
tgcggacgcg cgcgccccgg ccacggccgc gcgctcgtc tcctggcctc ccgcgcccgc      1200
tacaaatggc ggccccggcg tcccctcctc actccgaagc ttcccggttg acgacctctc     1260
cggtctcccc cctcacccca ccgcaacccg ggacgtcttc catggccgcc gccgccgccg     1320
cccccgccta ctaaaccacc ctacccaccc cctccaaact cccacacatt acatccttca     1380
aagagagcat cacacacaca cacacaccag cctagcgatc acatttccac gatgacgacg     1440
acgacgcgag tggcggccgc cgccgccggc gtgctgctgg tggcggcggc gctggccggc     1500
gtggcgcgcg gcgaggaccc gtacgtgttc ttcgagtgga aggtgacgta cggcaccaag     1560
accctcctgg acgcgccgca aaggtgatc ctgatcaacg gcgagttccc gggcccgcgg      1620
atcaactgct cgtccaacaa caacatcgtg gtgaacgtgt caaccagct ggacgagccg      1680 ctgctcttca cctggaacgg gatgcagcac cgcaagaact cgtggcagga cggcctcgcc     1740
gggacgcagt gccccatcgc gccgggcacc aactacacgt acaagtggca gcccaaggac     1800
cagatcggca gcttcttcta cttcccgtcg ctggggatgc accgcgccgc cggcggctac     1860
ggcgggatca gcgtcgtcag ccgcctgctc atcccggtcc cgttcgaccc gccggccgac     1920
gaccacatgg tgctcatcgg cgactggtac accaaggacc acgccgccat ggccaagatg     1980
ctcgacgccg gcaagagctt cggccgcccg cacggggtgg tcatcaacgg caagtccggc     2040
aaggccgccg ccgacccgcc catgttcacc gtcgaggccg gcaagacgta ccggctccgc     2100
gtctgcaacg tcggcatcaa ggcgtcgctc aacttccgca tccagggcca cgacatgaag     2160
ctggtggaga tggagggctc ccacacggtg caggacatgt acgactccct cgacgtccac     2220
gtcggccact gcctctccgt cctcgtcgac gccgaccaga agcccggcga ctactacgcg     2280
gtggcgtcca cgcggttcat ccacgaggcc aagtcggtgt cagccgtcat ccgctacgcc     2340
ggctcgagca cgccgccgtc gccggccgtg ccggagccgc cggcgggatg ggcgtggtcg     2400
atcaaccagt ggaggtcgtt ccggtggaac ctgacggcga gcgccgcccg ccccaacccg     2460
caggggtcct accactacgg ccagatcaac atcacgcgca ccatcaggct catggtctcc     2520
cggggccaca tcgacggcaa gctcaagtac ggcttcaatg gcgtctccca cgtcgacgcc     2580
gagacgccgc tcaagctcgc cgagtacttc aacgtcaccg acggcgtctt caggtacaac     2640
cagatgaccg acgtgccgcc cgccgtcaat ggccccctcc acgtcgtccc caacgtcatc     2700
accgccgagt tccgcacctt catcgagatc atcttcgaga accccgagaa gagcatggac     2760
tccgtccacc tcgacggcta cgccttcttc gccgtcgggt acgtacatac atcgccccc      2820 attactacta cctccattaa cctttttatta aagataggct tggccattca ttttattttt     2880
aaaaaattat ataagtatca tctattttat tgtaatttga tttatcgtca agtgtgcttt     2940
aaacataatt tgattttttt tatatttgca taaaaaattg aatattatga atgatgtata     3000
```

```
tgatctgata ctactgttaa ctaacttact gatgcgcata ataataaaat ttttaataa      3060 gacgaatgat ataaaaaaag tttttaaat tacctccatt tataatatac gatgttttt       3120 ttacttttaa cattcgttta taatatatgt tttttcacaa acgtttgagt tttgaccatt     3180
tattttattt aaaaataatt atgcagttat catctatttt attgtaattt tattgtaatt    3240
tgattattgt cgagtgtact ttaaaatacga tttgatttt ctatatttac ataaaatttt    3300
taaataagat aaatgatgga tacgatctga tgctaccgtt gactgactga ctgatggcgc   3360
aggatggggc cggggaagtg gtcggcggag gagaggaaga cgtacaacct gctggacggg   3420
gtgagccggc actcggtcca ggtgtacccg aggtcgtgga cggcgatcat gctgacgttc   3480
gacaacgccg ggatgtggaa cgtgaggtcc aacatctggg agaggcacta cctcggcgag   3540
cagctctaca tcagcgtcgt ctcgccggcg aggtcgctcc gggacgagta caacatgccg   3600
gagaacgccc tccgctgcgg caaggtcgtc ggcctgccgc tgccgccgtc ctacctcccg   3660
gcctaattca tcgatcgatg catatatgta ctgaacccga tgacattctt ctcttgttct   3720
tgacattttt tgtgatcttt tgcttaatct ggcgaaataa tcaacttaat ttgggctcgt   3780
gcttattgca tgtccccgcg aaaagaagaa caaaagagga gtggaaactg aaacgtacgt   3840
cctatgaaga agctgagcgc cgtcgtcgtc agctggatgt aatttcgata tgccctctaa   3900
aaaccattgt aatggtggag ttatattata catatgattt catcgctcac atatatatat   3960
atatatatat atatatatat atatatatat atatatacta                         4000

<210> SEQ ID NO 5
<211> LENGTH: 32
<212> TYPE: DNA
<213> ORGANISM: Artificial
<220> FEATURE:
<223> OTHER INFORMATION: oligonucleotide primer TSOL109

<400> SEQUENCE: 5
ggaagatctg atatcgtagt tttgtgatag tt                                    32

<210> SEQ ID NO 6
<211> LENGTH: 30
<212> TYPE: DNA
<213> ORGANISM: Artificial
<220> FEATURE:
<223> OTHER INFORMATION: oligonucleotide primer TSOL119

<400> SEQUENCE: 6
gtcgtaccat ggtggaaatg tgatcgctag                                       30

<210> SEQ ID NO 7
<211> LENGTH: 1137
<212> TYPE: DNA
<213> ORGANISM: Oryza sativa
<220> FEATURE:
<221> NAME/KEY: promoter region
<222> LOCATION: (16)..(1127)
<220> FEATURE:
<221> NAME/KEY: transcription start site
<222> LOCATION: (932)..(932)
<220> FEATURE:
<221> NAME/KEY: transcription start site
<222> LOCATION: (940)..(940)
<220> FEATURE:
<221> NAME/KEY: translation initiation codon
<222> LOCATION: (1128)..(1130)

<400> SEQUENCE: 7
```

-continued

```
ggaagatctg atatcgtagt tttgtgatag tttggttata atatctgtag ttttatgaaa      60
tttactcttt tcgtcttcac tgcaatttgg aatgatggaa ttgactagat ccggcattac     120
cgatgggctg ccgaacgctg tgatgcggtt gatcttgagc gatccgggac gccacaagca     180
ccgatgggtt ctgggagttc atacggctgg tgcagcagtg tgtcaatagc agccgggatg     240
tgcgcccaac catggtcgcc gtcgagagga ggatcgaaga catcctgaac tcggttgtca     300
ggtcatccac caccgggttc atgactgccg gaggcgacac acccagcaac gagccaaatc     360
gtgaagataa cggaaacgag ccaaatccca gcaacgagat cgccagggac tagtagtacg     420
tacagcagtg gtgatttgtc atataggtgt atatcggctg ttttcgcatc tcaaggcctc     480
aagcagtgtg tgcaatctgg agtagtatat aaatatgtaa aatgttcatt tcgatatact     540
gtcaaatgcg tgtaaattaa ccaatgctaa acaacacac tgtgactaaa tttactgagt      600
tggatgatga ggatgattat gttgcgtgca cacctgatca ggaggacata taatataggc     660
catttgggcc gtcttggaca ccaccgtttg atctgtatga agttgggccg aactatgcaa     720
gcccagaggc gctgcctctg tgccacggcc cacgggcatc gctggatggt caagcaggtg     780
atcggtggag cgccaatggc ggcggcgaga cacacagcgc ggcgcgcgcg cgaacgtgcg     840
gacgcgcgcg ccccggccac ggccgccgcg ctcgtctcct ggcctcccgc gcccgctaca     900 aatgcggcc ccggcgtccc ctcctcactc cgaagcttcc cggttgacaa cctctccggt      960 ctccccctc accccaccgc aacccgggac gtcttccatg gccgccgccg ccgccgcccc     1020
cgcctactaa accaccctac ccaccccctc caaactccca cacattacat ccttcaaaga    1080
gagcatcaca cacacacaca caccagccta gcgatcacat ttccaccatg gtacgac       1137
```

<210> SEQ ID NO 8
<211> LENGTH: 1671
<212> TYPE: DNA
<213> ORGANISM: Oryza sativa
<220> FEATURE:
<221> NAME/KEY: CDS
<222> LOCATION: (1)..(1671)

<400> SEQUENCE: 8

```
atg acg acg acg acg cga gtg gcg gcc gcc gcc gcc ggc gtg ctg ctg     48
Met Thr Thr Thr Thr Arg Val Ala Ala Ala Ala Ala Gly Val Leu Leu
1               5                   10                  15 gtg gcg gcg gcg ctg gcc ggc gtg gcg cgc ggc gag gac ccg tac gtg     96
Val Ala Ala Ala Leu Ala Gly Val Ala Arg Gly Glu Asp Pro Tyr Val
            20                  25                  30 ttc ttc gag tgg aag gtg acg tac ggc acc aag acc ctc ctg gac gcg    144
Phe Phe Glu Trp Lys Val Thr Tyr Gly Thr Lys Thr Leu Leu Asp Ala
        35                  40                  45 ccg cag aag gtg atc ctg atc aac ggc gag ttc ccg ggc ccg cgg atc    192
Pro Gln Lys Val Ile Leu Ile Asn Gly Glu Phe Pro Gly Pro Arg Ile
    50                  55                  60 aac tgc tcg tcc aac aac aac atc gtg gtg aac gtg ttc aac cag ctg    240
Asn Cys Ser Ser Asn Asn Asn Ile Val Val Asn Val Phe Asn Gln Leu
65                  70                  75                  80 gac gag ccg ctg ctc ttc acc tgg aac ggg atg cag cac cgc aag aac    288
Asp Glu Pro Leu Leu Phe Thr Trp Asn Gly Met Gln His Arg Lys Asn
                85                  90                  95 tcg tgg cag gac ggc ctc gcc ggg acg cag tgc ccc atc gcg ccg ggc    336
Ser Trp Gln Asp Gly Leu Ala Gly Thr Gln Cys Pro Ile Ala Pro Gly
            100                 105                 110 acc aac tac acg tac aag tgg cag ccc aag gac cag atc ggc agc ttc    384
Thr Asn Tyr Thr Tyr Lys Trp Gln Pro Lys Asp Gln Ile Gly Ser Phe
```

```
                    -continued
       115               120              125
ttc tac ttc ccg tcg ctg ggg atg cac cgc gcc gcc ggc ggc tac ggc    432
Phe Tyr Phe Pro Ser Leu Gly Met His Arg Ala Ala Gly Gly Tyr Gly
    130             135              140 ggg atc agc gtc gtc agc cgc ctg ctc atc ccg gtc ccg ttc gac ccg    480
Gly Ile Ser Val Val Ser Arg Leu Leu Ile Pro Val Pro Phe Asp Pro
145             150              155              160 ccg gcc gac gac cac atg gtg ctc atc ggc gac tgg tac acc aag gac    528
Pro Ala Asp Asp His Met Val Leu Ile Gly Asp Trp Tyr Thr Lys Asp
                165              170              175 cac gcc gcc atg gcc aag atg ctc gac gcc ggc aag agc ttc ggc cgc    576
His Ala Ala Met Ala Lys Met Leu Asp Ala Gly Lys Ser Phe Gly Arg
        180              185              190 ccg cac ggg gtg gtc atc aac ggc aag tcc ggc aag gcc gcc gcc gac    624
Pro His Gly Val Val Ile Asn Gly Lys Ser Gly Lys Ala Ala Ala Asp
            195              200              205 ccg ccc atg ttc acc gtc gag gcc ggc aag acg tac cgg ctc cgc gtc    672
Pro Pro Met Phe Thr Val Glu Ala Gly Lys Thr Tyr Arg Leu Arg Val
    210             215              220 tgc aac gtc ggc atc aag gcg tcg ctc aac ttc cgc atc cag ggc cac    720
Cys Asn Val Gly Ile Lys Ala Ser Leu Asn Phe Arg Ile Gln Gly His
225             230              235              240 gac atg aag ctg gtg gag atg gag ggc tcc cac acg gtg cag gac atg    768
Asp Met Lys Leu Val Glu Met Glu Gly Ser His Thr Val Gln Asp Met
                245              250              255 tac gac tcc ctc gac gtc cac gtc ggc cac tgc ctc tcc gtc ctc gtc    816
Tyr Asp Ser Leu Asp Val His Val Gly His Cys Leu Ser Val Leu Val
        260              265              270 gac gcc gac cag aag ccc ggc gac tac tac gcg gtg gcg tcc acg cgg    864
Asp Ala Asp Gln Lys Pro Gly Asp Tyr Tyr Ala Val Ala Ser Thr Arg
            275              280              285 ttc atc cac gag gcc aag tcg gtg tca gcc gtc atc cgc tac gcc ggc    912
Phe Ile His Glu Ala Lys Ser Val Ser Ala Val Ile Arg Tyr Ala Gly
    290             295              300 tcg agc acg ccg ccg tcg ccg gcc gtg ccg gag ccg ccg gcg gga tgg    960
Ser Ser Thr Pro Pro Ser Pro Ala Val Pro Glu Pro Pro Ala Gly Trp
305             310              315              320 gcg tgg tcg atc aac cag tgg agg tcg ttc cgg tgg aac ctg acg gcg   1008
Ala Trp Ser Ile Asn Gln Trp Arg Ser Phe Arg Trp Asn Leu Thr Ala
                325              330              335 agc gcc gcc cgc ccc aac ccg cag ggg tcc tac cac tac ggc cag atc   1056
Ser Ala Ala Arg Pro Asn Pro Gln Gly Ser Tyr His Tyr Gly Gln Ile
        340              345              350 aac atc acg cgc acc atc agg ctc atg gtc tcc cgg ggc cac atc gac   1104
Asn Ile Thr Arg Thr Ile Arg Leu Met Val Ser Arg Gly His Ile Asp
            355              360              365 ggc aag ctc aag tac ggc ttc aat ggc gtc tcc cac gtc gac gcc gag   1152
Gly Lys Leu Lys Tyr Gly Phe Asn Gly Val Ser His Val Asp Ala Glu
    370             375              380 acg ccg ctc aag ctc gcc gag tac ttc aac gtc acc gac ggc gtc ttc   1200
Thr Pro Leu Lys Leu Ala Glu Tyr Phe Asn Val Thr Asp Gly Val Phe
385             390              395              400 agg tac aac cag atg acc gac gtg ccg ccc gcc gtc aat ggc ccc ctc   1248
Arg Tyr Asn Gln Met Thr Asp Val Pro Pro Ala Val Asn Gly Pro Leu
                405              410              415 cac gtc gtc ccc aac gtc atc acc gcc gag ttc cgc acc ttc atc gag   1296
His Val Val Pro Asn Val Ile Thr Ala Glu Phe Arg Thr Phe Ile Glu
        420              425              430 atc atc ttc gag aac ccc gag aag agc atg gac tcc gtc cac ctc gac   1344
Ile Ile Phe Glu Asn Pro Glu Lys Ser Met Asp Ser Val His Leu Asp
```

```
Ile Ile Phe Glu Asn Pro Glu Lys Ser Met Asp Ser Val His Leu Asp
        435                 440                 445 ggc tac gcc ttc ttc gcc gtc ggg atg ggg ccg ggg aag tgg tcg gcg     1392
Gly Tyr Ala Phe Phe Ala Val Gly Met Gly Pro Gly Lys Trp Ser Ala
450                 455                 460 gag gag agg aag acg tac aac ctg ctg gac ggg gtg agc cgg cac tcg     1440
Glu Glu Arg Lys Thr Tyr Asn Leu Leu Asp Gly Val Ser Arg His Ser
465                 470                 475                 480 gtc cag gtg tac ccg agg tcg tgg acg gcg atc atg ctg acg ttc gac     1488
Val Gln Val Tyr Pro Arg Ser Trp Thr Ala Ile Met Leu Thr Phe Asp
            485                 490                 495 aac gcc ggg atg tgg aac gtg agg tcc aac atc tgg gag agg cac tac     1536
Asn Ala Gly Met Trp Asn Val Arg Ser Asn Ile Trp Glu Arg His Tyr
        500                 505                 510 ctc ggc gag cag ctc tac atc agc gtc gtc tcg ccg gcg agg tcg ctc     1584
Leu Gly Glu Gln Leu Tyr Ile Ser Val Val Ser Pro Ala Arg Ser Leu
    515                 520                 525 cgg gac gag tac aac atg ccg gag aac gcc ctc cgc tgc ggc aag gtc     1632
Arg Asp Glu Tyr Asn Met Pro Glu Asn Ala Leu Arg Cys Gly Lys Val
530                 535                 540 gtc ggc ctg ccg ctg ccg ccg tcc tac ctc ccg gcc taa                 1671
Val Gly Leu Pro Leu Pro Pro Ser Tyr Leu Pro Ala
545                 550                 555

<210> SEQ ID NO 9
<211> LENGTH: 556
<212> TYPE: PRT
<213> ORGANISM: Oryza sativa

<400> SEQUENCE: 9

Met Thr Thr Thr Thr Arg Val Ala Ala Ala Ala Gly Val Leu Leu
1               5                   10                  15

Val Ala Ala Leu Ala Gly Val Ala Arg Gly Glu Asp Pro Tyr Val
            20                  25                  30

Phe Phe Glu Trp Lys Val Thr Tyr Gly Thr Lys Thr Leu Leu Asp Ala
        35                  40                  45

Pro Gln Lys Val Ile Leu Ile Asn Gly Glu Phe Pro Gly Pro Arg Ile
    50                  55                  60

Asn Cys Ser Ser Asn Asn Asn Ile Val Val Asn Val Phe Asn Gln Leu
65                  70                  75                  80

Asp Glu Pro Leu Leu Phe Thr Trp Asn Gly Met Gln His Arg Lys Asn
                85                  90                  95

Ser Trp Gln Asp Gly Leu Ala Gly Thr Gln Cys Pro Ile Ala Pro Gly
            100                 105                 110

Thr Asn Tyr Thr Tyr Lys Trp Gln Pro Lys Asp Gln Ile Gly Ser Phe
        115                 120                 125

Phe Tyr Phe Pro Ser Leu Gly Met His Arg Ala Ala Gly Gly Tyr Gly
    130                 135                 140

Gly Ile Ser Val Val Ser Arg Leu Leu Ile Pro Val Pro Phe Asp Pro
145                 150                 155                 160

Pro Ala Asp Asp His Met Val Leu Ile Gly Asp Trp Tyr Thr Lys Asp
                165                 170                 175

His Ala Ala Met Ala Lys Met Leu Asp Ala Gly Lys Ser Phe Gly Arg
            180                 185                 190

Pro His Gly Val Val Ile Asn Gly Lys Ser Gly Lys Ala Ala Ala Asp
        195                 200                 205

Pro Pro Met Phe Thr Val Glu Ala Gly Lys Thr Tyr Arg Leu Arg Val
```

-continued

```
                  210                 215                 220
Cys Asn Val Gly Ile Lys Ala Ser Leu Asn Phe Arg Ile Gln Gly His
225                 230                 235                 240

Asp Met Lys Leu Val Glu Met Glu Gly Ser His Thr Val Gln Asp Met
                245                 250                 255

Tyr Asp Ser Leu Asp Val His Val Gly His Cys Leu Ser Val Leu Val
            260                 265                 270

Asp Ala Asp Gln Lys Pro Gly Asp Tyr Tyr Ala Val Ala Ser Thr Arg
        275                 280                 285

Phe Ile His Glu Ala Lys Ser Val Ser Ala Val Ile Arg Tyr Ala Gly
    290                 295                 300

Ser Ser Thr Pro Pro Ser Pro Ala Val Pro Glu Pro Ala Gly Trp
305                 310                 315                 320

Ala Trp Ser Ile Asn Gln Trp Arg Ser Phe Arg Trp Asn Leu Thr Ala
                325                 330                 335

Ser Ala Ala Arg Pro Asn Pro Gln Gly Ser Tyr His Tyr Gly Gln Ile
            340                 345                 350

Asn Ile Thr Arg Thr Ile Arg Leu Met Val Ser Arg Gly His Ile Asp
        355                 360                 365

Gly Lys Leu Lys Tyr Gly Phe Asn Gly Val Ser His Val Asp Ala Glu
    370                 375                 380

Thr Pro Leu Lys Leu Ala Glu Tyr Phe Asn Val Thr Asp Gly Val Phe
385                 390                 395                 400

Arg Tyr Asn Gln Met Thr Asp Val Pro Ala Val Asn Gly Pro Leu
                405                 410                 415

His Val Val Pro Asn Val Ile Thr Ala Glu Phe Arg Thr Phe Ile Glu
            420                 425                 430

Ile Ile Phe Glu Asn Pro Glu Lys Ser Met Asp Ser Val His Leu Asp
        435                 440                 445

Gly Tyr Ala Phe Phe Ala Val Gly Met Gly Pro Gly Lys Trp Ser Ala
    450                 455                 460

Glu Glu Arg Lys Thr Tyr Asn Leu Leu Asp Gly Val Ser Arg His Ser
465                 470                 475                 480

Val Gln Val Tyr Pro Arg Ser Trp Thr Ala Ile Met Leu Thr Phe Asp
                485                 490                 495

Asn Ala Gly Met Trp Asn Val Arg Ser Asn Ile Trp Glu Arg His Tyr
            500                 505                 510

Leu Gly Glu Gln Leu Tyr Ile Ser Val Val Ser Pro Ala Arg Ser Leu
        515                 520                 525

Arg Asp Glu Tyr Asn Met Pro Glu Asn Ala Leu Arg Cys Gly Lys Val
    530                 535                 540

Val Gly Leu Pro Leu Pro Pro Ser Tyr Leu Pro Ala
545                 550                 555

<210> SEQ ID NO 10
<211> LENGTH: 4000
<212> TYPE: DNA
<213> ORGANISM: Oryza sativa
<220> FEATURE:
<221> NAME/KEY: transcription start site
<222> LOCATION: (1147)..(1147)
<220> FEATURE:
<221> NAME/KEY: transcription start site
<222> LOCATION: (1155)..(1155)
<220> FEATURE:
<221> NAME/KEY: n
<222> LOCATION: (1171)..(1270)
```

-continued

```
<223> OTHER INFORMATION: any nucleotide
<220> FEATURE:
<221> NAME/KEY: Intron
<222> LOCATION: (2659)..(3221)
<220> FEATURE:
<221> NAME/KEY: polyA_site
<222> LOCATION: (3806)..(3806)
<220> FEATURE:
<221> NAME/KEY: polyA_site
<222> LOCATION: (3809)..(3809)

<400> SEQUENCE: 10
```

| | | | | | |
|---|---|---|---|---|---|
| gggaacaaat | gtaagtatat | tggtcgttta | gccctatgca | tctcacgggt | tgttaatatt   60 |
| agccatatga | attttggtaa | taggaacagg | ttgtttatac | ctatttctga | caatcagacg  120 |
| agacaaaata | tacctatttc | tgtgtgtcaa | cataaaaacc | ttatcaaatt | gagcatgcta  180 |
| atttgatcat | atcctgttag | gcttatatgg | agccggagta | caagaggaca | gggcgattgt  240 |
| cggacaagat | tgacgtgtac | agctttggga | tagtgatgat | ggagctggtg | atcaagaacg  300 |
| atgtgatgcg | gtcgatcttg | agcgacctgc | cgaatggggt | gcccaacaat | gtgatgcggt  360 |
| tgatcttgag | cgacctgcca | gccgatccat | ctgacgacca | tgaacccac | acgagcatac  420 |
| tggacgacat | cgtcgaccca | gcgatccggg | atgtgcgccc | aaccatggtc | gccgtcgaga  480 |
| ggaggatcga | agacatcctg | aactcagttg | tcaggtcatc | caccaccgag | ttcatgactg  540 |
| ccggaggcga | cacacccatc | aacgagccaa | atcgtgaaga | taacggaaac | gagccaaatc  600 |
| ccagcaacga | gatcgccagg | gactagtacg | tacagcagtg | gtgatttgtc | ataggtgt  660 |
| gtatatcggc | tgttttcgca | tctcaaggcc | tcaagcagtg | tgtgcaatct | ggagtagtat  720 |
| ataaatatgt | aaaatgttca | tttcgatata | ctgtcaaatg | cgtgtaaatt | aaccaatgct  780 |
| aaaacaacac | actgtgacta | aatttactga | gttggatgat | gaggatgatt | atgttgcgtg  840 |
| cacacctgat | caggaggaca | tataatatag | gccatatggg | ccgtcttgga | caccaccgtt  900 |
| tgatttgtgt | gaagttgggc | cgaactatgc | aagcccagag | gcgctgcctc | tgtgccacgg  960 |
| cccacgggca | ccgctggatg | gtcaagcagg | tgatcggtgg | agcgccaatg | gcggcggcga 1020 |
| gacacagctc | ggcgcgcgcg | cgcgaacgtg | cggacgcgcg | cgccccggcc | acggccgcgg 1080 |
| ccgcgctcgt | ctcctggcct | cccgcgcccg | ctacaaatgg | cggccccggc | gtcccctcct 1140 |
| cactccgaag | cttcccggtt | gacgacctct | nnnnnnnnnn | nnnnnnnnnn | nnnnnnnnnn 1200 |
| nnnnnnnnnn | nnnnnnnnnn | nnnnnnnnnn | nnnnnnnnnn | nnnnnnnnnn | nnnnnnnnnn 1260 |
| nnnnnnnnnn | ctagcgacca | ctcgacgcgg | cgacgatgac | gacgacgcga | atggcggccg 1320 |
| ccgccgccgg | cgtgctgctg | gtggcggtgg | cgctggccgg | cgtggcgcgc | ggcgaggacc 1380 |
| cgtacgtgtt | cttcgagtgg | aaggtgacgt | acggcaccaa | gaccctcctg | gacgcgccgc 1440 |
| agaaggtgat | cctgatcaac | ggcgagttcc | cgggcccgcg | gatcaactgc | tcgtccaaca 1500 |
| acaacatcgt | ggtgaacgtg | ttcaaccagc | tggacgagcc | gctgctcttc | acctggaacg 1560 |
| ggatgcagca | ccgcaagaac | tcgtggcagg | acggcctcgc | cgggacgcag | tgccccatcg 1620 |
| cgccgggcac | caactacacg | tacaagtggc | agcccaagga | ccagatcggc | agcttcttct 1680 |
| acttcccgtc | gctggggatg | caccgcgccg | ccggcggcta | cggcgggatc | agcgtcgtca 1740 |
| gccgcctgct | catcccggtc | ccgttcgacc | gccggccga | cgaccacatg | gtgctcatcg 1800 |
| gcgactggta | caccaaggat | cacgccgcca | tggccaagat | gctcgacgcc | ggcaagagct 1860 |
| tcggccgccc | gcacggggtg | gtcatcaacg | gcaagtccgg | caaggccgcc | gccgacccgc 1920 |
| ccatgttcac | cgtcgaggcc | ggcaagacgt | accggctccg | cgtctgcaac | gtcggcatca 1980 |

-continued

```
aggcgtcgct caacttccgc atccagggcc acgacatgaa gctggtggag atggagggct    2040
cccacacggt gcaggacatg tacgactccc tcgacgtcca cgtcggccac tgcctctccg    2100
tcctcgtcga cgccgaccag aagcccggcg actactacgc ggtggcgtcc acgcggttca    2160
tccacgaggc caagtcggtg tcagccgtca tccgctacgc cggctcgagc acgccgccgt    2220
cgccggccgt gccggagccg ccggcgggat gggcgtggtc gatcaaccag tggaggtcgt    2280
tccggtggaa cctgacggcg agcgccgccc gccccaaccc gcaggggtcc taccactacg    2340
gccagatcaa catcacgcgc accatcaggc tcatggtctc ccggggccac atcgacggca    2400
agctcaagta cggcttcaat ggcgtctccc acgtcgacgc cgagacgccg ctcaagctcg    2460
ccgagtactt caacgtcacc gacggcgtct tcaggtacaa ccagatgacc gacgtgccgc    2520
ccgccgtcaa tggccccctc cacgtcgtcc ccaacgtcat caccgccgag ttccgcacct    2580
tcatcgagat catcttcgag aaccccgaga agagcatgga ctccgtccac ctcgacggct    2640
acgccttctt cgccgtcggg tacgtacata catcgccccc cattactact acctccatta    2700
acctttatt aaagataggc ttggccattc attttatttt taaaaaatta tataagtatc    2760
atctatttta ttgtaatttg atttatcgtc aagtgtgctt taaacataat ttgattttt    2820
tttatatttg cataaaaaat tgaatattat gaatgatgta tacgatctga tactactgtt    2880
aactaactga ctgatgcgca taataataaa ttttttaat aagacgaatg atataaaaaa    2940
gtttttaaa ctatctccat ttataatata cgatgttttt ttactttaa cattcgttta    3000
taatatatgt tttttcacat acgtttgagt tttgaccatt tattttattt aaaaataatt    3060
atgcagttat catctatttt attgtaattt tattgtaatt tgattattgt cgagtgtgct    3120
ttaaatacaa tttgattttt ctatatttac ataaaatttt taaataagat aaatgatgga    3180
tacgatctga tgctaccgtt gactgactga ctgatggcgc aggatggggc cggggaagtg    3240
gtcggcggag gagaggaaga cgtacaacct gctggacggg gtgagccggc actcggtcca    3300
ggtgtacccg aggtcgtgga cggcgatcat gctgacgttc gacaacgccg ggatgtggaa    3360
cgtgaggtcc aacatctggg agaggcacta cctcggcgag cagctctaca tcagcgtcgt    3420
ctcgccggcg aggtcgctcc gggacgagta caacatgccg gagaacgccc tccgctgcgg    3480
caaggtcgtc ggcctgccgc tgccgccgtc ctacctcccg gcctaattca tcgatcgatg    3540
catatatgta ctgaacccga tgacattctt ctcttgttct tgacattttt tgtgatcttt    3600
tgcttaatct ggcgaaataa tcaacttaat ttgggctcgt gcttattgca tgtccccgcg    3660
aaaagaagaa caaagagga gtggaaactg aaacgtacgt cctaggaaga agctgagcgc    3720
cgtcgtcgtc agctggatgt aatttcgata tgccctctaa aaaccattgt aatggtggag    3780
ttatattata catgatttt catcgctcac atatatatat atatatatat atatatatac    3840
tagctactga tgagttaaaa aaaccccccat tttttttca agtgtgatta atttatcatt    3900
atttgtcagt cgatgttttt ttcaatctta cgaattacgt ttgaaatcga atgacctgta    3960
gctcaagccc tacccatcta cacgatggga gtgtttaaga                         4000
```

US 7,667,097 B2

RICE POLLEN-PREFERENTIAL PROMOTERS AND USES THEREOF

CROSS-REFERENCE TO RELATED APPLICATIONS

This application is a U.S. national stage application of International Application No. PCT/EP2005/004000, filed on Apr. 13, 2005, which claims the benefit of U.S. Provisional Application Ser. No. 60/561,878, filed on Apr. 14, 2004, the disclosures of each of which are herein incorporated by reference in their entireties.

BACKGROUND OF THE INVENTION

1. Field of the Invention

The invention relates to the isolation of promoters from rice capable of directing transcription of an operably linked foreign DNA sequence preferentially in microspores and/or pollen of plants, such as rice plants. The invention also relates to the use of chimeric genes for the preferential expression of biologically active RNA of interest in microspores and/or pollen of plants, such as rice plants. Plants, such as rice plants, comprising rice pollen-preferential promoters operably linked to a foreign DNA sequence which upon transcription yield biologically active RNA preferentially in microspores and/or pollen of said plants are also provided.

2. Description of Related Art

Promoters that can provide gene expression preferentially in microspores and/or pollen of a plant and thereby provide little or no gene expression in other parts of the plant are useful in the production of transformed plants, in which a gene is to be expressed preferentially in microspores and/or pollen. The promoters can for example be used to create pollen-lethality genes and maintainer genes as described in WO 93/25695 (which is incorporated herein by reference.

A pollen-specific cDNA clone from *Nicotiana tabacum*, designated as NTPc303, has been isolated and characterized by Weterings et al. (1992), *Plant Mol Biol* 18:1101-1111. The first NTP303 transcripts are detectable on northern blot at the early bi-nucleate state and accumulate until the pollen has reached maturity. During germination and pollen tube growth in vitro new NTP303 transcripts appear. The corresponding promoter, designed NPT303 promoter, has been isolated and characterized by Weterings et al., (1995), *Plant J* 8:55-63. The 5'-untranslated region of the NTP303 gene was characterized by Hulzink et al., (2002), *Plant Physiol* 129:342-353.

A genomic clone, named Bp10, of *Brassica napus* has been isolated and characterized by Albani et al. (1992), *Plant J* 2:331-342. Bp10 contains a member of a small pollen-specific gene family. The expression of the Bp10 gene family is maximal in early bi-nucleate microspores and declines considerably in mature tri-nucleate pollen.

A pollen-specific cDNA from *Zea mays* inbred line W-22, designated as Zmc13, has been isolated and characterized by Hanson et al. (1989), *The Plant Cell* 1:173. The corresponding genomic clone, designated as Zmg13, containing substantial portions of the 5' flanking region has been isolated and characterized by Hamilton et al. (1989), *Sex Plant Reprod* 2:208 (see also Hamilton et al. (1992), *Plant Mol Biol* 18:211). A corresponding promoter region from *Zea mays* inbred line H99 was isolated as described in WO 93/25695.

Three pollen-expressed genes (LAT52, LAT56 and LAT59) from tomato were characterized by McCormick et al. (1991), *Symp Soc Exp Biol* 45:229-244. LAT52 encodes a protein that shows amino acid sequence similarity to the protein encoded by the pollen-specific cDNA clone Zmc13 isolated from maize. The proteins encoded by LAT56 and LAT59 genes show significant sequence similarity to bacterial pectate lyases and to a fungal pectin lyase. Twell et al. (1991), *Genes Dev* 5:496-507, investigated the functional organization and properties of cis regulatory elements in the promoter regions of the LAT 52 and LAT59 genes that are preferentially and coordinately expressed during pollen maturation and demonstrated that only minimal (less than 200 bp) promoter proximal regions are required for developmentally regulated expression in pollen and in specific cell types of the sporophyte. They identified two upstream regions in the LAT52 promoter and further showed that a 19 bp segment from one of those regions enhanced expression of the heterologous CaMV35S promoter in pollen. Eyal et al (1995), *Plant Cell* 7:373-384, further identified 30 bp proximal regions of LAT 52 and LAT 59 that are essential for their expression in pollen and that confer pollen specificity when fused to the heterologous CaMV35S core promoter. Adjacent upstream elements, the 52/56 box in LAT52 and the 56/59 box in LAT59, are involved in modulating the level of expression in pollen.

Xu et al. (1999) *Proc Natl Acad Shi USA* 96:2554-2558 identified and characterized a gene from Lily, LGC1, which was shown to be expressed exclusively in the male gametic cells. Singh et al. (2003), FEBS Left 542:47-52, report that a 0.8 kb promoter sequence upstream of the start of the transcription site of the generative cell-specific LGC1 gene is sufficient to regulate the expression of reporter genes in a cell-specific manner and identified −242 bp as the minimal sequence necessary for male gametic cell-specific expression. In addition, a regulatory sequence required for determining generative cell-specific expression of LGC1 was identified.

Despite the fact that pollen-preferential promoters are available in the art, a need remains for alternative promoters capable of preferential expression in microspores and/or pollen of a plant, e.g. for the independent expression of several foreign DNA sequences of interest without the possibility of post-transcriptional silencing due to the use of the same promoter. In addition, the known pollen-preferential promoters, each direct a particular temporal, spatial and/or developmental expression pattern, which does not always suit particular goals. There remains thus a need for novel pollen-preferential promoters with the capacity to control transcription in microspores and/or pollen of a plant.

SUMMARY AND OBJECTS OF THE INVENTION

It is an object of the invention to provide rice pollen-preferential promoter regions comprising the following nucleotide sequence:

a) a nucleotide sequence of about 400 basepairs (bp) to about 1110 bp which can be amplified from the genomic DNA of a plant, such as a monocotyledonous plant, including a rice plant, using a set of primers, comprising at least 15 consecutive nucleotides complementary to the nucleotide sequence of SEQ ID No 4 from the nucleotide at position 320 to the nucleotide at position 1431; or b) a nucleotide sequence of about 1110 bp which can be amplified from the genomic DNA of a plant, such as a monocotyledonous plant, including a rice plant, using a set of primers, the first of which comprising the nucleotide sequence of SEQ ID No 5 from the nucleotide at position 16 to the nucleotide at position 32, the second of which comprising the complement of the nucleotide sequence of SEQ ID No 6 from the nucleotide at position 12 to the nucleotide at position 30; or c) the nucleotide sequence of SEQ ID No 7 from the nucleotide at position 16 to the nucleotide at position 1126, or parts thereof having promoter activity; or d) the nucleotide sequence of SEQ ID No 7 from the nucleotide at position 16 to the nucleotide at position 1127, or parts thereof having promoter activity; or e) the nucleotide sequence of SEQ ID No 7 from the nucleotide at position is 231 to the nucleotide at position 955, or parts thereof having promoter activity; or f) the nucleotide sequence of SEQ ID No 4 from the nucleotide at position 320 to the nucleotide at position 1431, or parts thereof having promoter activity; or g) the nucleotide sequence of SEQ ID No 4 from the nucleotide at position 320 to the nucleotide at position 1430, or parts thereof having promoter activity; or h) the nucleotide sequence SEQ ID No 4 from the nucleotide at position 537 to the nucleotide at position 1259, or parts thereof having promoter activity; or i) the nucleotide sequence of SEQ ID No 10 from the nucleotide at position 444 to the nucleotide at position 1170, or parts thereof having promoter activity; or j) a nucleotide sequence having at least 90%, or at least 95%, or 96%, 97%, 98%, 99% sequence identity with, or is identical to any of said nucleotide sequence mentioned under a), b), c), d), e), f), g), h) or i); or k) a nucleotide sequence of about 400 bp to about 1100 bp hybridizing under stringent conditions with a DNA fragment having said nucleotide sequence mentioned under a), b), c), d), e), f), g), h), I) or j).

It is another object of the invention to provide chimeric genes comprising the following operably linked DNA regions: a rice pollen-preferential promoter or promoter region according to the invention: a heterologous DNA region encoding a biologically active RNA of interest; and a transcription termination and polyadenylation signal active in plant cells.

The biologically active RNA may encode a protein of interest, such as a protein which when expressed in the microspores and/or pollen cells of a plant results in nonfunctional pollen. The biologically active RNA may also be an antisense, sense or double stranded RNA useful for post-transcriptional silencing of a target gene of interest, such as a gene endogenous to a plant, the product of which is essential for the normal development of pollen.

Also provided are plant cells and plants, such as monocotyledonous plants, including cereal plants, such as rice, or seeds thereof comprising a chimeric gene according to the invention.

It is yet another objective to provide a method for expressing a biologically active RNA preferentially in microspores and/or pollen of a plant, comprising the steps of: providing the microspores and/or pollen cells of said plants with a chimeric gene according to the invention; and growing the plants.

The invention further provides the use of a rice pollen-preferential promoter region according to the invention for preferential expression of a biologically active RNA in microspores and/or pollen of a plant.

It is yet another object of the invention to provide isolated DNA molecules, encoding mRNAs which are preferentially expressed in mature anthers of a plant, or microspores and/or pollen of a plant, from which cDNAs can be prepared comprising the following nucleotide sequence:

a) a nucleotide sequence hybridizing under stringent conditions with a nucleotide sequence comprising about 180 bp which can be amplified from the genomic DNA of a plant, such as a monocotyledonous plant, including a rice plant, using a set of primers, comprising at least 15 consecutive nucleotides complementary to the nucleotide sequence of SEQ ID No 3; or b) a nucleotide sequence hybridizing under stringent conditions with a nucleotide sequence comprising about 180 bp or 180 bp which can be amplified from the genomic DNA of a plant, such as a monocotyledonous plant, including a rice plant, using a set of primers, the first of which comprising the nucleotide sequence of SEQ ID No 1 from the nucleotide at position 10 to the nucleotide at position 29, the second of which comprising the complement of the nucleotide sequence of SEQ ID No 2 from the nucleotide at position 12 to the nucleotide at position 31; or c) a nucleotide sequence hybridizing under stringent conditions with a nucleotide sequence comprising the nucleotide sequence of SEQ ID No 3; or d) a nucleotide sequence having at least 90%, 96%, 97%, 98%, 99% sequence identity with, or is identical to, the nucleotide sequence of SEQ ID No 3; or e) a nucleotide sequence having at least 70%, 74%, 75%, 76%, 77%, or 78% sequence identity with, or is identical to, the nucleotide sequence of SEQ ID No 3 from the nucleotide at position 49 to the nucleotide at position 180.

Also provided are isolated DNA molecules, encoding mRNAs which are preferentially expressed in microspores and/or pollen of a plant, comprising the following nucleotide sequence:

a) the nucleotide sequence of SEQ ID No 4 from the nucleotide at position 2128 to the nucleotide at position 2543; or b) the nucleotide sequence of SEQ ID No 4 from the nucleotide at position 1236 or 1244 to the nucleotide at position 3946 or 3949, or parts thereof encoding a pollen-preferential mRNA; or c) the nucleotide sequence of SEQ ID No 4 from the nucleotide at position 1437 to the nucleotide at position 3950, or parts thereof encoding a pollen-preferential mRNA; or d) the nucleotide sequence of SEQ ID No 10 from the nucleotide at position 1298 to the nucleotide at position 3810, or parts thereof encoding a pollen-preferential mRNA; or e) the nucleotide sequence of SEQ ID No 10 from the nucleotide at position 1147 or 1155 to the nucleotide at position 3806 or 3809, or parts thereof encoding a pollen-preferential mRNA; or f) a nucleotide sequence having at least 90%, 95%, 96%, 97%, 98%, or 99% sequence identity with, or is identical to, any one of the nucleotide sequences mentioned under a), b), c), d) or e); or g) a nucleotide sequence hybridizing under stringent conditions with any one of the nucleotide sequences mentioned under a), b), c), d), e) or f).

Further provided are isolated DNA molecules, encoding proteins that are preferentially expressed in microspores and/or pollen of a plant, comprising the following nucleotide sequence:

a) the nucleotide sequence of SEQ ID No 4 from the nucleotide at position 1474 to the nucleotide at position 2796; or b) the nucleotide sequence of SEQ ID No 4 from the nucleotide at position 1432 to the nucleotide at position 3666, or parts thereof encoding a pollen-preferential protein; or c) the nucleotide sequence of SEQ ID No 4 from the nucleotide at position 1432 to the nucleotide at position 2797; or d) the nucleotide sequence of SEQ ID No 4 from the nucleotide at position 3362 to the nucleotide at position 3666; or e) the nucleotide sequence of SEQ ID No 8; or
f) a nucleotide sequence encoding a polypeptide with the amino acid sequence of SEQ ID No 9; or
g) the nucleotide sequence of SEQ ID No 10 from the nucleotide at position 1293 or 1296 to the nucleotide at position 3526, or parts thereof encoding a pollen-preferential protein; or
h) the nucleotide sequence of SEQ ID No 10 from the nucleotide at position 1293 or 1296 to the nucleotide at position 2658; or
i) the nucleotide sequence of SEQ ID No 10 from the nucleotide at position 3222 to the nucleotide at position 3526; or
j) a nucleotide sequence having at least 90%, 95%, 96%, 97%, 98%, or 99% sequence identity with, or is identical to, any one of the nucleotide sequences mentioned under a), b), c), d), e), f), g), h), or i); or
k) a nucleotide sequence hybridizing under stringent conditions with any one of the nucleotide sequences mentioned under a), b), c), d), e), f), g), h), i), j).

The invention further provides the use of the isolated DNA molecules for the isolation of a rice pollen-preferential promoter or promoter region. Also provided is the use of the isolated DNA molecules for post-transcriptional silencing of a target gene of interest, such as the rice pollen-preferential genes of this invention or functional homologues thereof.

In yet another embodiment, the invention provides a method for isolating a rice pollen-preferential promoter or promoter region, comprising the steps of:
identifying a genomic fragment comprising the isolated DNA molecules encoding mRNAs which are preferentially expressed in mature anthers of a plant, or microspores and/or pollen of a plant, or encoding a protein which is preferentially expressed in microspores and/or pollen of a plant, such as a rice plant, and
isolating a DNA region upstream of said genomic DNA fragment.

Also provided are rice pollen-preferential promoters and promoter regions obtained by this method.

DETAILED DESCRIPTION OF PREFERRED EMBODIMENTS

Figure 1:
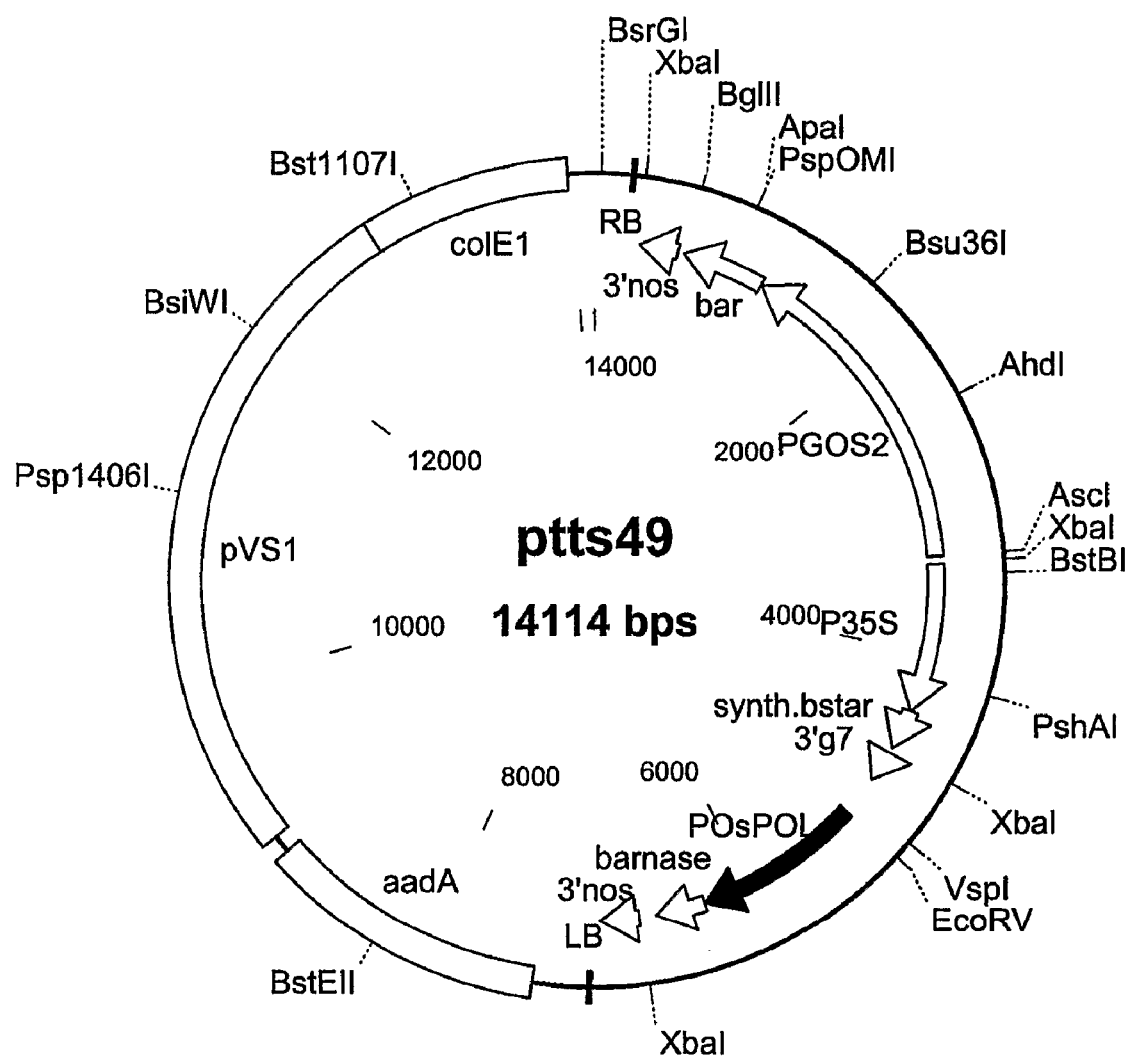
FIG. 1: Schematic representation of pTTS49.
LB: T-DNA left border sequence
3'nos: 3' untranslated region of the nopaline synthase gene from *Agrobacterium tumefaciens* [Depicker et al. (1982) *Journal of Molecular and Applied Genetics* 1: 561-573];
barnase: coding sequence of the barnase gene of *Bacillus amyloliquifaciens* [Hartley (1988) *J Mol Biol* 202, 913];
POsPOL: rice pollen-preferential promoter region;
3'g7: 3' untranslated region of gene 7 from *Agrobacterium tumefaciens* [Dhaese et al. (1983) *The EMBO J* 2: 419];
Synth bstar: coding sequence of improved barstar protein as described in WO98/10081;
P35S: promoter region of the 35S transcript of CaMV [Odell et al. (1985) *Nature* 313: 810-812]
PGOS2: promoter region of the gos2 gene of rice [de Pater et al. (1992) *The Plant J* 2: 837];
bar: coding sequence of the bialaphos resistance gene of *Streptomyces hygroscopicus* [Thompson et al (1987) *The EMBO Journal* 6: 2519-2523];
3'nos: 3' untranslated region of the nopaline synthase gene of *Agrobacterium tumefaciens* [Depicker et al. (1982) supra];
RB: T-DNA right border sequence
colE1: origin of replication from pMB1 for stable maintenance in *E. coli* [Alting-Mees et al. (1992) *Meth Enzymol* 216: 483-495]
pVS1: stability and replication functions of the *Pseudomonas aeruginosa* pVS1 plasmid (Deblaere et al. (1987) In R Wu, L Grossman, eds, Recombinant DNA: Part D. Methods in Enzymology, Vol 153. Academic Press, New York, pp 277-292];
aadA: aminoglycoside adenyltransferase gene conferring resistance to streptomycin and spectinomycin [Tolmasky and Crosa (1993) *Plasmid* 29:31-40; Fling et al. (1985) *Nucl Acids Res* 13:7095]

The invention is based on the finding that the promoters and promoter regions described herein are particularly suited for the preferential expression (i.e. transcription or transcription and translation) of an operably linked foreign DNA in microspores and/or pollen of plants, such as monocotyledonous plants, including cereal plants such as rice, corn and wheat.

In one embodiment of the invention, rice pollen-preferential promoter regions are provided comprising the nucleotide sequence of SEQ ID No 7 from the nucleotide at position 16 to the nucleotide at position 1126 or 1127.

As used herein "rice" refers to *Oryza* species, like *Oryza sativa*, including japonica, indica and javanica cultivar groups; whether soil, water, upland, rainfed shallow, deep water, floating or irrigated.

As used herein, the term "promoter" denotes any DNA that is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA, that is involved in driving transcription and controlling (i.e., regulating) the timing, location (tissue- or cell-type) and level of transcription of a given DNA sequence, such as a DNA coding for a protein or polypeptide. "Regulatory regions" include developmentally regulated, tissue preferential, inducible and constitutive regulatory elements. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within the plant as well, such regulatory elements are considered "tissue preferential". "Regulatory regions" may be found either upstream, within, downstream, or a combination thereof, of the coding region of a gene. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription 3' end formation (and/or regulation) signals, including one or more polyadenylation signals.

The term "gene" means any nucleotide sequence comprising a DNA region (the "transcribed DNA region") that is transcribed into an RNA molecule (e.g., a mRNA) in a cell under control of suitable regulatory regions, e.g., a plant expressible promoter region. A gene may thus comprise several operably linked DNA fragments such as a promoter, a 5' untranslated leader sequence, a coding region, and a 3' untranslated region comprising a polyadenylation site. An endogenous plant gene is a gene that is naturally found in a plant species. A chimeric gene is any gene that is not normally found in a plant species or, alternatively, any gene in which the promoter is not associated in nature with part or all of the transcribed DNA region or with at least one other regulatory-region of the gene.

The term "expression of a gene" refers to the process wherein a DNA region under control of regulatory regions, such as the promoter, is transcribed into an RNA which is biologically active, i.e., which is either capable of interaction with another nucleic acid or which is capable of being translated into a biologically active polypeptide or protein. A gene is said to encode an RNA when the expression of the gene results in a biologically active RNA, such as an antisense RNA, a sense RNA, a double-stranded RNA or a ribozyme (such RNA can encode a protein or not). A gene is said to encode a protein when the end product of the expression of the gene is a biologically active protein or polypeptide.

The term "pollen-preferential", with respect to the expression of a DNA in accordance with this invention, refers to the specific expression of a DNA in microspores and/or pollen of plants, such as rice plants ("rice pollen-preferential"). For practical purposes, pollen-preferential expression of a DNA means, for example, that transcripts can be detected in RNA isolated from mature anthers, or microspores and/or pollen of plants, while transcript levels of the DNA in tissues different from mature anthers, or microspores and/or pollen, such as but not limited to callus, roots, leaves, spikelets of 1-6 mm, mature green spikelets, immature anthers, basis of spikelets, panicle axis, are either below detection or very low.

It will be clear that having read these embodiments, the person skilled in the art can easily identify and use functional equivalent promoters for the same purposes.

DNA sequences that have a promoter activity substantially similar to rice pollen-preferential promoter regions comprising the nucleotide sequence of SEQ ID No 7 from the nucleotide at, position 16 to the nucleotide at position 1126 or 1127, or parts thereof having promoter activity, are functional equivalents of these promoters. These functional equivalent promoters may hybridize with the rice pollen-preferential promoter regions comprising the nucleotide sequence of SEQ ID No 7 from the nucleotide at position 16 to the nucleotide at position 1126 under stringent hybridization conditions.

"Stringent hybridization conditions" as used herein means that hybridization will generally occur if there is at least 95% or at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as fish sperm DNA, followed by washing the hybridization support in 0.1×SSC at approximately 65° C. for about 10 min to 30 min. Other stringent hybridization and wash conditions are well known and are exemplified in Sambrook et al., Molecular Cloning: A Laboratory Manual, Second Edition, Cold Spring Harbor, N.Y. (1989), particularly in chapter 11.

Other functional equivalent promoters comprise nucleotide sequences which can be amplified using oligonucleotide primers comprising at least about 15 to 30, or at least about 20, or at least about 25, or at least about 50, or at least about 100 consecutive nucleotides selected from the nucleotide sequence of SEQ ID No 4 from the nucleotide at position 320 to the nucleotide at position 1431 or selected from the nucleotide sequence of SEQ ID No 7 from the nucleotide at position 16 to the nucleotide at position 1127, in a polymerase chain amplification reaction. Examples of such oligonucleotide primers are TSOL109 (SEQ ID No 5) and TSOL119 (SEQ ID No 6).

Functionally equivalent promoter may be isolated e.g. from different rice varieties. They may also be made by modifying isolated rice pollen-preferential promoters through addition, substitution, deletion or insertion of nucleotides. They can also be completely or partly synthesized.

Alternatively, functional equivalent promoters may be isolated using a cDNA of a transcript which is expressed in microspores and/or pollen of a plant, such as a rice plant, as a probe to isolate the genomic DNA upstream of the nucleotide sequence corresponding to the nucleotide sequence of the cDNA.

As used herein "cDNA" is used to indicate both the first strand cDNA (complementary to the mRNA) as well as the strand complementary thereto (and thus identical to the mRNA except that U is replaced by T) or a double stranded cDNA fragment.

In accordance with this invention, rice pollen preferential cDNAs and their corresponding plant genomic DNA fragments may be identified as follows:

1) A cDNA library may be constructed starting from mRNA isolated from microspores and/or pollen, or from anthers at different stages of microsporogenesis (e.g. from anthers of spikelets of different lengths whereby the spikelet length can be correlated with the developmental stage of the spikelet or with the stage of microsporogenesis e.g. as indicated in Table I), or from spikelets at different stages of microsporogenesis (see e.g. Table I).

This cDNA library may be subjected to differential screening in order to identify a mRNA which is preferentially present in microspores and/or pollen, or in anthers or spikelets at one stage of microsporogenesis (e.g. stage VIII to X; Table I) when compared to anthers or spikelets of another stage of microsporogenesis (e.g. stage I to VII; Table I) and to other plant tissues including but not limited to: callus, roots, leaves, basis of spikelets, panicle axis, immature, mature and germinating seeds, and the like.

Alternatively, the cDNA library may be screened with oligonucleotides, which are reverse translated from a determined amino acid sequence of an isolated protein that has been identified to be preferentially present in microspores and/or pollen. Furthermore, it is possible to use the same oligonucleotides in a nested polymerase chain reaction (PCR) approach and to use the amplified fragment(s) as a probe to screen the library.

The cDNA library can be constructed from a pool of mRNAs, e.g. isolated from microspores, pollen, anthers or, spikelets at different stages of microsporogenesis.

One method to identify and isolate the 3' ends of cDNA of RNA preferentially or selectively expressed in a specific tissue such as here microspores and/or pollen of plants, is the so-called READS analysis ["Restriction Endonucleolytic Analysis of Differentially expressed Sequences" as described e.g. by Prashar and Weismann (1999), *Methods Enzymol* 303:258-272, or U.S. Pat. No. 5,712,126 (both documents are herein incorporated by reference)].

2) a cDNA reverse transcribed from RNA preferentially transcribed in microspores and/or pollen of plants, such as rice plants, or 3' ends of cDNAs identified by READS differential display analysis as expressed preferentially in microspores and/or pollen of plants may be isolated and further characterized by e.g. nucleotide sequence determination; a full length cDNA may be isolated using e.g. 5' RACE (rapid amplification of cDNA ends) technology.

3) this cDNA or the 3' end thereof may be used as a probe to identify and isolate the region in the plant genome, comprising the nucleotide sequence encoding the rice pollen-preferential mRNA. Alternatively, the genomic DNA can be isolated, by e.g. inverse polymerase chain reaction (PCR) using oligonucleotides deduced from the cDNA sequence. Alternatively, TAIL-PCR (thermal asymmetric interlaced PCR as described by Liu et al. (1995) *Genomics* 25:674-681, using nested long specific oligonucleotides derived from the nucleotide sequence of the (5' end) of the identified cDNA and a short arbitrary degenerate primer may be used to isolate the genomic sequences flanking the coding region.

4) optionally, RNA probes corresponding to the cDNAs are constructed and used in conventional RNA-RNA in situ hybridization analysis [see e.g., De Block et al. (1993), *Anal Biochem* 215: 86] of different plant tissues, including anthers or spikelets at different stages of microsporogenesis, to confirm the preferential presence of the mRNA produced by the endogenous plant gene presumed pollen-preferential expression in microspores and/or pollen.

TABLE I

Developmental stages of spikelets and corresponding stage of microsporogenesis

| Developmental stage of spikelet | Approximate spikelet length | Stage of microsporogenesis |
|---|---|---|
| Stage I | <1.0 mm | Sporogenous tissue |
| Stage II | 1.0-1.5 mm | Sporogenous cell develops into microsporocytes |
| Stage III | 1.5-2.0 mm | Microsporocytes separate from each other, followed by callose deposition |
| Stage IV | 2.0-2.5 mm | Microsporocytes enter meiosis |
| Stage V | 2.5-3.5 mm | Microsporocytes in meiosis |
| Stage VI | 3.5-4.0 mm | Microsporocytes at end of meiosis |
| Stage VII | 4.0-4.5 mm | Tetrad - very young microspores (cytoplasmic, nucleus centrally placed) |
| Stage VIII | 4.5-5.0 mm | Uninucleate microspores |
| Stage IX | 5.0-5.5 mm | Binucleate microspores |
| Stage X | 5.5-6.0 mm (white) | Pollen grains half starch-filled |
| Stage XI | >6.0 mm (green) | Pollen grains starch-filled |

Once the rice pollen-preferential gene (i.e., the genomic DNA fragment, encoding the rice pollen-preferential mRNA from which the rice pollen-preferential cDNA can be prepared) is obtained, the promoter region containing the rice pollen-preferential promoter is determined as the region upstream (i.e., located 5' of) from codon coding for the first amino acid of the protein encoded by the mRNA. It is preferred that such promoter region is at least about 400 to 500 bp, or at least about 1000 bp, 1100 bp, or 1110 bp, or at least about 1200 bp to 1300 bp, or at least about 1300 to 1500 bp, or at least about 1500 to 2000 bp, or at least 400 bp, 500 bp, 1000 bp, 1100 bp, 1110 bp, 1200 bp, 1300 bp, 1500 bp, or 2000 bp upstream of the start codon. For convenience, it is preferred that such promoter region does not extend more than about 3000 to 5000 bp upstream of the start codon. The size fragment may be partially determined by the presence of convenient restriction sites. The actual rice pollen-preferential promoter is the region of the genomic DNA upstream (i.e., 5') of the region encoding the rice pollen-preferential mRNA. A chimeric gene comprising a rice pollen-preferential promoter operably linked to the coding region of a marker gene will produce the marker protein preferentially the microspores and/or pollen of the transgenic rice plants, which can be assayed e.g. by conventional in situ histochemical techniques.

Examples of rice pollen-preferential genes from which rice pollen-preferential promoters can be obtained, are genes encoding a mRNA which can be detected preferentially in mature anthers of rice, or in anthers of rice spikelets of more than 4.5 mm (Table I), or in microspores and/or pollen, by hybridization to an RNA probe complementary to the nucleotide sequence of SEQ ID No 3.

One embodiment of a rice pollen-preferential gene of the present invention, is a gene encoding a mRNA from which a cDNA can be prepared comprising the nucleotide sequence of SEQ ID No 8, or comprising a nucleotide sequence encoding a polypeptide with the amino acid sequence of SEQ ID No 9.

Other rice pollen-preferential genes from which rice pollen-preferential promoters can be obtained, are genes comprising the nucleotide sequence of SEQ ID No 4 from the nucleotide at position 1236, 1244 or 1432 to the nucleotide at position 3666, 3946 or 3949, or parts thereof encoding a pollen-preferential mRNA.

Still other rice pollen-preferential genes from which rice pollen-preferential promoters can be obtained, are genes comprising the nucleotide sequence of SEQ ID No 10 from the nucleotide at position 1147, 1155, 1293 or 1296 to the nucleotide at position 3526, 3806, or 3809, or parts thereof encoding a pollen-preferential mRNA.

One embodiment of a promoter region of the present invention is a promoter region contained in the 5' regulatory region of a genomic clone comprising the nucleotide sequence of SEQ ID No 4 from the nucleotide at position 1432 to the nucleotide at position 3666, e.g. the 5' regulatory region with the nucleotide sequence of SEQ ID No 4 from the nucleotide at position 320 to the nucleotide at position 1431 or the 5' regulatory region with the nucleotide sequence of SEQ ID No 7 from the nucleotide at position 16 to the nucleotide at position 1127.

Such a promoter region comprises a rice pollen-preferential promoter of the invention and the 5' untranslated leader region, and may be used for the construction of pollen-preferential chimeric genes, such as rice pollen-preferential chimeric genes. However, smaller DNA fragments can be used as promoter regions in this invention and it is believed that any fragment from the nucleotide sequence of SEQ ID No 4 from the nucleotide at position 320 to the nucleotide at position 1431 or from the nucleotide sequence of SEQ ID No 7 from the nucleotide at position 16 to the nucleotide at position 1127, which comprises at least 400 basepairs upstream from the translation initiation codon can be used.

Artificial promoters can be constructed which contain those internal portions of the rice pollen-preferential promoter region of SEQ ID No 7 that determine the rice pollen-preference of this promoter. These artificial promoters might contain a "core promoter" or "TATA box region" of another promoter capable of expression in plants, such as a CaMV 35S "TATA box region" as described in WO 93/19188. The suitability of promoter regions containing such artificial promoters may be identified by their appropriate fusion to a reporter gene and the detection of the expression of the reporter gene in the appropriate tissue(s) and at the appropriate developmental stage. It is believed that such smaller promoters and/or artificial promoters comprising those internal portions of rice pollen-preferential promoter region of SEQ ID No 7 that determine the rice pollen-preference can provide better selectivity of transcription in microspores and/or pollen of plants and/or provide enhanced levels of transcription of the transcribed regions of the rice pollen-preferential chimeric genes of the invention. Such smaller portions of the rice pollen-preferential promoter regions of the invention may include nucleotide sequences, which share a high homology between the promoter region of SEQ ID No 7 and other known pollen-preferential promoters.

Besides the actual promoter, the 5' regulatory region of the rice pollen-preferential genes of this invention also comprises a DNA fragment encoding a 5' untranslated leader (5'UTL) sequence of an RNA located between the transcription start site and the translation, start site. It is believed that 5' transcription start sites are located at position 932 or 940 in SEQ ID No 7, at position 1236 or 1244 in SEQ ID No 4, and at position 1147 or 1155 in SEQ ID No 10 resulting in a 5'UTL of about 196 to 188 nucleotides in length. It is also believed that this region can be replaced by another 5'UTL, such as the 5'UTL of another plant-expressible gene, without substantially affecting the specificity of the promoter.

Thus, in another embodiment, the invention provides rice pollen-preferential promoters comprising the following nucleotide sequence:
a) a nucleotide sequence of about 210 bp to about 920 bp which can be amplified from the genomic DNA of a plant, such as a monocotyledonous plant, including a rice plant, using a set of primers, comprising at least 15 consecutive nucleotides complementary to the nucleotide sequence of SEQ ID No 4 from the nucleotide at position 320 to the nucleotide at position 1236 or 1244; or
b) the nucleotide sequence of SEQ ID No 7 from the nucleotide at position 16 to the nucleotide at position 932 or 940, or parts thereof having promoter activity; or
c) the nucleotide sequence of SEQ ID No 7 from the nucleotide at position 231 to the nucleotide at position 932 or 940, or parts thereof having promoter activity; or
d) the nucleotide sequence of SEQ ID No. 4 from the nucleotide, at position 320 to the nucleotide at position 1236 or 1244, or parts thereof having promoter activity; or
e) the nucleotide sequence of SEQ ID No 4 from the nucleotide at position 537 to the nucleotide at position 1236 or 1244, or parts thereof having promoter activity; or
f) the nucleotide sequence of SEQ ID No 10 from the nucleotide at position 444 to the nucleotide at position 1147 or 1155, or parts thereof having promoter activity; or
g) a nucleotide sequence having at least 90%, or at least 95%, or 96%, 97%, 98%, 99% sequence identity with, or is identical to any of said nucleotide sequence mentioned under a), b), c), d), e), or f); or
h) a nucleotide sequence of about 210 bp to about 920 bp hybridizing under stringent conditions with a DNA fragment having said nucleotide sequence mentioned under a), b), c), d), e), f), or g).

For the purpose of this invention, the "sequence identity" of two related nucleotide or amino acid sequences, expressed as a percentage, refers to the number of positions in the two optimally aligned sequences which have identical residues (×100) divided by the number of positions compared and the "sequence conservation" of two related nucleotide or amino acid sequences, expressed as a percentage, refers to the number of positions in the two optimally aligned sequences which preserve the physico-chemical properties of the original residue. A gap, i.e. a position in an alignment where a residue is present in one sequence but not in the other, is regarded as a position with non-identical residues.

To calculate sequence identify between two sequences for the purpose of this invention, the Align Plus program (provided by Scientific & Educational Software, USA) can be used. Two sequences are compared by searching for regions of local homology with the Needleman-Wunsch method (match score, mismatch penalty and gap penalty set to one) or by aligning the two sequences using a global alignment procedure (For nucleotides the default scoring matrix used is "standard linear" with mismatch penalty=2, open gap penalty=4 and extend gap penalty=1 for DNA. For proteins the default scoring matrix is "blosum 62".). Alternatively, the sequence identity between two sequences is determined with the Basic Local Alignment Search Tool (BLAST; Altschul et al. (1990), *J Mol Biol* 215:403-410; Altschul and Gish (1996), Meth Enzymol 266:460-480). A BLAST search is performed with the following default parameters: cost to open gap=5 for nucleotides/11 for amino acids, cost to extend gap=2 for nucleotides/1 for proteins, penalty for nucleotide mismatch=−3, reward for nucleotide match=1. The default matrix is blosum 62.

It goes without saying that promoters and promoter regions of the invention may also comprise (or may be provided with) additional elements known to improve transcription efficiency such as enhancers, introns, e.g. introns in the 5'UTL, etc. These additional elements can also be present in the transcribed region of the pollen-preferential genes of this invention.

The invention further includes DNA molecules comprising the rice pollen-preferential promoters of the invention operably linked to one or more heterologous regions coding for a biologically active RNA, peptide or protein. The promoters of the invention may be used to express any heterologous coding region desired.

Thus in another embodiment of the invention, a chimeric gene is provided comprising
1) a rice pollen-preferential promoter region comprising
   a) a nucleotide sequence of about 400 bp to about 1110 bp which can be amplified from the genomic DNA of a plant, such as a monocotyledonous plant, including a rice plant, using a set of primers, comprising at least 15 consecutive nucleotides complementary to the nucleotide sequence of SEQ ID No 4 from the nucleotide at position 320 to the nucleotide at position 1431; or
   b) a nucleotide sequence of about 1110 bp which can be amplified from the genomic DNA of a plant, such as a monocotyledonous plant, including a rice plant, using a set of primers, the first of which comprising the nucleotide sequence of SEQ ID No 5 from the nucleotide at position 16 to the nucleotide at position 32, the second of which comprising the complement of the nucleotide sequence of SEQ ID No 6 from the nucleotide at position 12 to the nucleotide at position 30; or
   c) the nucleotide sequence of SEQ ID No 7 from the nucleotide at position 16 to the nucleotide at position 1126, or parts thereof having promoter activity; or
   d) the nucleotide sequence of SEQ ID No 7 from the nucleotide at position 16 to the nucleotide at position 1127, or parts thereof having promoter activity; or
   e) the nucleotide sequence of SEQ ID No 7 from the nucleotide at position 231 to the nucleotide at position 955, or parts thereof having promoter activity; or
   f) the nucleotide sequence of SEQ ID No 4 from the nucleotide at position 320 to the nucleotide at position 1431, or parts thereof having promoter activity; or
   g) the nucleotide sequence of SEQ ID No 4 from the nucleotide at position 320 to the nucleotide at position 1430, or parts thereof having promoter-activity; or h) the nucleotide sequence of SEQ ID No 4 from the nucleotide at position 537 to the nucleotide at position 1259, or parts thereof having promoter activity; or i) the nucleotide sequence of SEQ ID No 10 from the nucleotide at position 444 to the nucleotide at position 1170, or parts thereof having promoter activity; or j) a nucleotide sequence having at least 90%, or at least 95%, or 96%, 97%, 98%, 99% sequence identity with, or is identical to any of said nucleotide sequence mentioned under a), b), c), d), e), f), g), h) or i); or k) a nucleotide sequence of about 400 bp to about 1100 bp hybridizing under stringent conditions with a DNA fragment having said nucleotide sequence mentioned under a), b), c), d), e), f), g), h), i) or j).

2) a DNA region of interest, which when transcribed yields a biologically active RNA; and 3) a DNA region comprising, a 3' transcription termination and polyadenylation signal functional in plant cells.

The DNA region of interest, or the transcribed DNA may thus encode a protein or polypeptide, but may also encode biologically active RNA, such as an antisense RNA, a sense RNA, or a double stranded RNA comprising both sense and antisense RNA stretches capable of basepairing and forming a double stranded RNA, as described in WO 99/53050 (incorporated herein by reference) usable for post-transcriptional gene silencing of a target sequence.

The DNA region of interest may encode for example a protein which when expressed in microspores and/or pollen of a plant results in non-functional pollen (called hereinafter "pollen-lethality DNA"). Suitable pollen-lethality DNA regions to be operably linked to the rice pollen-preferential promoters of the invention include any DNA region, whose expression product (RNA and/or protein or polypeptide) in microspores and/or pollen of the plant disturbs significantly their metabolism, functioning and/or development.

Examples of pollen-lethality DNAs are described in WO 93/25695, for example those DNAs encoding: RNases (WO 89/10396) such as RNaseT1 from *Aspergillus oryzae* (Quaas et al. (1988) *Eur J Biochem* 173:617) or barnase from *Bacillus amyloliquifaciens* (Hartley (1988) *J Mol Biol* 202:913); DNases such as endonucleases (e.g., EcoRI); proteases such as papain; enzymes which catalyze the synthesis of phytohormones (e.g., isopentenyl transferase or the gene products of gene 1 and gene 2 of the T-DNA of *Agrobacterium*); glucanases; lipases, lipid peroxidases; plant cell wall inhibitors; or toxins (e.g., the A-fragment of diphtheria toxin or botulin). Other examples of pollen-lethality DNAs are DNAs encoding an antisense, a sense, or a double-stranded RNA molecule capable of reducing the expression of a gene endogenous to a plant, the products of which are essential for the normal development of fertile pollen. Further examples of pollen-lethality DNAs encode ribozymes capable of cleaving specifically given target sequences of genes encoding products that are essential for the normal development of fertile pollen. Still other examples of pollen-lethality DNAs encode products that can render pollen, and not other parts of the plant—susceptible to specific diseases (e.g. fungi or virus infection) or stress conditions (e.g. herbicides).

Depending on the nature of the pollen-lethality DNA, the host organism can be provided, on the same or a different plasmid from that containing the pollen-lethality DNA or on its chromosomal DNA, with another DNA sequence that prevents or inhibits the effect of the expression of the pollen-lethality DNA in tissues other than microspores and/or Pollen in the host organism (as described in WO 96/26283). Such another DNA sequence encode, for example: an antisense RNA so that the accumulation and translation of the pollen-lethality RNA is prevented; or a protein (e.g., barstar) which specifically inhibits the gene product of the pollen-lethality DNA (e.g., barnase; Hartley (1988) *J Mol Biol* 202, 913).

In another embodiment of the invention, a chimeric gene is provided comprising 1) a plant expressible promoter or promoter region;

2) a DNA, encoding an RNA molecule comprising a first and second RNA region wherein
   a) the first RNA region comprises a nucleotide sequence of at least 19 consecutive nucleotides having about 94% sequence identity to the nucleotide sequence of an endogenous gene, such as the pollen-preferential genes of the present invention;
   b) the second RNA region comprises a nucleotide sequence complementary to the 19 consecutive nucleotides of the first RNA region; and
   c) the first and second RNA region are capable of base-pairing to form a double stranded RNA molecule between at least the 19 consecutive nucleotides of the first and second region;

3) a DNA region comprising a 3' transcription termination and polyadenylation signal functional in plant cells.

wherein the chimeric gene, when expressed in microspores and/or pollen of a plant, such as a monocotyledonous plant, including a rice plant, reduces the expression of said endogenous gene compared to the expression of said endogenous gene in an untransformed plant, such as an untransformed monocotyledonous plant.

By coupling a marker gene, such as a dominant herbicide resistance gene (for example, the bar gene coding for phosphinothricin acetyl transferase (PAT) that converts herbicidal phosphinothricin to a non-toxic compound [De Block et al. (1987) *EMBO J* 6:2513], to the chimeric genes of the invention, it becomes possible to select for uniform populations of plants containing the chimeric genes.

The invention further provides methods for expressing a foreign DNA of interest preferentially in the microspores and/or pollen of a plant, such as a rice plant, comprising the following steps:

a) providing plant cells with the pollen-preferential chimeric genes of the invention, which can be stably integrated in their genome, such as their nuclear genome, to generate transgenic cells;

b) regenerating plants from said transgenic cells.

A convenient way to provide plant cells with the chimeric genes of the invention is to introduce the DNA via conventional transformation methods. It will be clear that the actual method of transforming the plants, such as monocotyledonous plants, including cereal plants like rice, has little importance for the currently described methods and several methods for introduction of foreign DNA into the genome of plant cells are described including but not limited to: *Agrobacterium*-mediated transformation [see e.g. for rice: Hiei et al. (1994) *Plant J* 6:271-282; Hiei et al. (1997) *Plant Mol Biol.* 35:205-218], electroporation (see e.g. for rice: U.S. Pat. No. 5,641,664 and U.S. Pat. No. 5,679,558, incorporated herein by reference), or bombardment (see e.g. for rice Christou et al. (1991) *Biotechnology* 9:957, incorporated herein by reference).

Operably linking the foreign DNA of interest to a rice pollen-preferential promoter according to the invention, may also be achieved by replacing the DNA naturally associated with the rice pollen-preferential promoter by homologous recombination, with the DNA of interest, provided that said DNA of interest comprises a homology region with the DNA normally associated with the rice pollen-preferential promoter. Methods for introducing DNA of interest into plant cell genome by homologous recombination are available (e.g. U.S. Pat. No. 5,744,336 incorporated herein by reference).

The obtained transformed plant can be used in a conventional breeding scheme to produce more transformed plants with the same characteristics or to introduce the chimeric gene for rice pollen-preferential expression according to the invention in other varieties of the same or related plant species, or in hybrid Plants. Seeds and processed and unprocessed grain obtained from the transformed plants contain the chimeric genes of the invention as a stable genomic insert and are also encompassed by the invention. "Processed grain", as used herein, refers to grain, which has been treated using one or several processes, particularly to grain processed to be used as feed or food. Processing of grain includes but is not limited to polishing, milling, parboiling, dehusking and the like.

For example, in order to produce more transformed plants containing a pollen-lethality DNA under the control of the pollen-preferential promoter of this invention ("pollen-lethality gene"), the obtained transformed plants can be selfed or used as female partners in a cross with plants not containing a pollen-lethality gene: 50% of the progeny plants will contain the pollen-lethality gene, 50% will not. Alternatively, the obtained transformed plants can be used as male partners in a cross with plants not containing a pollen-lethality gene: none of the progeny plants will contain the pollen-lethality DNA.

Plants containing a pollen-lethality gene linked to a fertility-restorer gene ("maintainer plants" as described in WO 93/25695; incorporated herein by reference) can, for example, be used to maintain male-sterile plants. When the male-fertile maintainer plants are crossed with a male-sterile parent plant, a minimum, or no, male-fertile offspring is produced, thereby minimizing or avoiding altogether the need to remove male-fertile offspring.

It will be appreciated that the means and methods of the invention are useful for rice, but may also be used in other plants with similar effects, such as in cereal plants including wheat, oat, barley, rye, corn, turfgrass, sorghum, millet or sugarcane plants.

The following non-limiting Examples describe the isolation of rice pollen-preferential promoters and promoter regions, and the construction of chimeric genes for preferential expression in rice pollen. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences represented in the sequence listing:
SEQ ID No 1: oligonucleotide primer TSOL22
SEQ ID No 2: oligonucleotide primer TSOL23
SEQ ID No 3: nucleotide sequence comprising a rice pollen-preferential transcribed DNA
SEQ ID No 4: nucleotide sequence comprising a rice pollen-preferential gene
SEQ ID No 5: oligonucleotide primer TSOL109
SEQ ID No 6: oligonucleotide primer TSOL-119
SEQ ID No 7: nucleotide sequence comprising a rice pollen-preferential promoter region
SEQ ID No 8: nucleotide sequence comprising a rice pollen-preferential coding sequence
SEQ ID No 9: amino acid sequence comprising a rice pollen-preferential protein
SEQ ID No 10: nucleotide sequence comprising a rice pollen-preferential gene

EXAMPLES

Example 1

Identification and Characterization of a Pollen-Preferential cDNA Sequence from Rice A pollen-specific gene from *Nicotiana tabacum*, designated as NTP303, has been isolated and characterized (Weterings et al. and Hulzink et al., supra). The protein sequence of NTP303 (accession number P29162) was used as a query in a BLAST search restricted to *Oryza sativa* and a BAC end sequence (accession number AQ577962) was identified. The BLAST results showed that translated nucleotides 116 to 367 of AQ577962 (593 nucleotides in length) show 57% sequence identity and 75% sequence conservation with amino acids 207 to 290 of P29162 (554 amino acids in length). AQ577962 is derived from leaf tissue of *Oryza sativa* japonica Nipponbare. It has not been described that AQ577962 encodes a rice pollen-preferential gene.

AQ577962 was used as a query in a BLAST search restricted to expressed sequence tags (EST) from *Oryza sativa* and identified two rice cDNA sequences (accession numbers BE041024 and C72996):
BE041024 (765 nucleotides in length) is a rice cDNA derived from 2 weeks old rice plants (*Oryza sativa* indica Pokkali) that were treated for 1 week with 150 mM NaCl and encodes a putative pectinesterase. The BLAST results showed that nucleotides 130 to 363 of AQ577962 show 97% sequence identity with nucleotides 281 to 515 of BE041024 and nucleotides 386 to 498 of AQ577962 show 93% sequence identity with nucleotides 521 to 633 of BE041024.
C72996 (464 nucleotides in length) is a rice cDNA derived from panicles of *Oryza sativa* japonica Nipponbare at flowering stage. The BLAST results showed that nucleotides 199 to 279 of AQ577962 show 83% sequence identity with nucleotides 21 to 101 of C72996.

It has not been described that BE041024 or C72996 encode a rice pollen-preferential gene.

Global DNA alignment of the BAC end sequence AQ577962 with cDNA sequences BE041024 and C72996 allowed to select a putative exon sequence corresponding to nucleotides 131 to 310 of AQ577962 (SEQ ID No 3), which shows 98% sequence identity with nucleotides 282 to 462 of BE041024 (177 of 180 matching nucleotides) and nucleotides 49 to 180 of SEQ ID No 3 show 76% sequence identity with nucleotides 1 to 132 of C72996 (100 of 132 matching nucleotides).

Primer TSOL22 (SEQ ID No 1) was designed based on the recognition site of restriction enzyme KpnI and nucleotides 1 to 20 of SEQ ID No 3. Primer TSOL23 (SEQ ID No 2) was designed based on the recognition site of restriction enzyme HindIII and nucleotides 162 to 180 of SEQ ID No 3. Primers TSOL22 and TSOL23 were used in a polymerase chain reaction (PCR) using genomic DNA of *Oryza sativa* japonica Nipponbare as a template.

Each PCR sample contained 1×PCR buffer, 1.5 U Taq polymerase, 5 pmol TSOL22 primer, 5 pmol TSOL23 primer and 100 ng genomic DNA in a total volume of 20 µl overlaid with mineral oil. The PCR buffer (1×) contained 45 mM tris-HCl pH 8.8, 11 mM ammonium sulfate, 4.5 mM magnesium chloride, β-mercaptoethanol, 4.5 mM EDTA pH8, 10 mM of each dNTP and 0.1 mg/ml BSA.

PCR cycles were as follows:

1 PCR cycle included a denaturation temperature of 92° C. for 3 min

5 PCR cycles included a denaturation temperature of 92° C. for 1 min, a primer annealing temperature, of 58° C. for 1 min and an extension temperature of 72° C. for 2 min.

22 PCR cycles included a denaturation temperature of 92° C. for 30 sec, a primer annealing temperature of 58° C. for 30 sec and an extension temperature of 72° C. for 1 min.

1 PCR cycle included an extension temperature of 72° C. for 10 min

A 200 bp PCR fragment was chloroform extracted and ethanol precipitated, redissolved in TE and digested with KpnI and HindIII. The restricted PCR product was purified from low melting agarose, and cloned into expression vector pGEM7Z+cut with KpnI and HindIII, resulting in plasmid pTS303. The DNA sequence of the insert was obtained by the dideoxy chain termination method and comprised the nucleotide sequence of SEQ ID No 3.

Plant material was harvested from different tissues of *Oryza sativa* japonica:

callus roots leaves spikelets (size 1-4, 5 mm; approximately stage I to VII; Table I)

spikelets (size 4, 5-6 mm; approximately stage VIII to, X; Table I)

mature green spikelets (approximately stage XI; Table I)

immature anthers (from spikelets of approximately stage I to VIII; Table I)

mature anthers (from spikelets of approximately stage VIII to XI; Table I)

basis of spikelets panicle axis immature seeds (approximately 48 hours after pollination)

mature seeds germinating seeds (approximately 3 days after germination)

Total RNA was extracted from various rice tissues and separated electrophoretically on a 1.5% agarose-formaldehyde denaturing gel according to Sambrook et al. (1989; supra). The RNA was transferred onto a nylon membrane (Hybond N; Amersham) using capillary transfer. Membranes were prehybridised for at least 2 hours at 65° C. in a buffer containing 5×SSC, 50% formamide, 0.5% SDS, 5×Denhardt's (diluted from 100× stock containing 2% BSA, 2% Ficoll and 2% PVP) and 100 μg/ml fish sperm DNA. A radio-labeled probe was generated using 100 ng of plasmid pTS303 cut with KpnI, [$^{32}$P] dCTP (Amersham) and the Riboprobe® Combination System SP6 RNA Polymerase (Promega). Hybridisation was carried out overnight at 65° C. in the same buffer after adding the probe. The blot was washed at least three times at 65° C., with the final wash in 0.1×SSC, 0.1% SDS for at least 15 min and exposed to a KODAK film with intensifying screens at −70° C.

Northern blot analysis revealed that RNA transcribed from pTS303 cut with KpnI hybridized to mRNA present in total RNA from mature anthers. The transcript could not be detected in RNA from callus, roots, leaves, spikelets of 1-6 mm, mature green spikelets, immature anthers, basis of spikelets, panicle axis, immature, mature and germinating seeds.

Example 2

Identification and Characterization of Pollen-Preferential Genes from *Oryza Sativa* Japonica and Indica Corresponding to the Rice Pollen-Preferential cDNA Sequence of Example 1

Using C72996 as a query in a BLAST search, an *Oryza sativa* japonica chromosome 5 clone has been identified (accession number AC093952). Nucleotides 20873 to 20458 of AC093952 (127642 nucleotides in length; nucleotides 2128 to 2543 of SEQ ID No 4) show 97% sequence identity with nucleotides 1 to 420 of C72996. Furthermore, translated nucleotides 21527 to 20205 of AC093952 (nucleotides 1474 to 2796 of SEQ ID No 4) show 59% sequence identity and 73% sequence conservation with amino acids 11 to 454 of P29162. It has not been described that AC093952 encodes a rice pollen-preferential gene.

SEQ ID No 4 (AC093952 from nucleotide 23000 to 19001) was used as a query in a BLAST search and a putative rice coding sequence (TIGR model temp id(s): 8353.m 03630; SEQ ID No 8) was identified (the encoded protein is represented in SEQ ID No 9).

Alignment of SEQ ID No 4 with SEQ ID No 8:

showed 100% sequence identity between nucleotides 1432 to 2797 of SEQ ID 4 and nucleotides 1 to 1366 of SEQ ID No 8, and 100% sequence identity between nucleotides 3362 to 3666 of SEQ ID 4 and nucleotides 1367 to 1671 of SEQ ID No 8; and identified a putative translation initiation codon between nucleotides 1432 and 1434 of SEQ ID No 4, and a putative codon sequence of the rice pollen-preferential gene between nucleotides 1432 and 3666 of SEQ ID No 4 with a putative intron sequence between nucleotides 2798 and 3361 of SEQ ID 4.

Alignment of SEQ ID No 4 with an *Oryza sativa* japonica Nipponbare cDNA clone (accession number AK108702) and *Oryza sativa* japonica Nipponbare cDNAs from panicle at flowering stage (accession numbers AU101215, AU093980, C72986 and AU172461) identified:

two putative transcription start sites at nucleotide positions 1236 and 1244 of SEQ ID No 4, and two putative polyadenylation sites at nucleotide positions 3946 and 3949 of SEQ ID No 4.

SEQ ID No 4 was used as a query in a BLAST search and a whole genome shotgun sequence from *Oryza sativa* indica (accession number AAAA01001318; 30064 nucleotides in length) was identified. It has not been described that AAAA01001318 encodes a rice pollen-preferential gene.

Alignment of SEQ ID No 4 with SEQ ID No 10 (nucleotides 6001 to 10000 of AAAA01001318):

showed 97% sequence identify between nucleotides 537 to 1259 of SEQ ID No 4 and nucleotides 444 to 1170 of SEQ ID No 10 (710 of 730 matching bases), and 99% sequence identity between nucleotides 1437 to 3950 of SEQ ID No 4 and nucleotides 1298 to 3810 of 6 SEQ ID No 10 (2500 of 2515 matching bases), identified two putative transcription start sites at nucleotide positions 1147 and 1155 of SEQ ID No 10, and two putative polyadenylation sites at nucleotide positions 3806 and 3809 of SEQ ID No 10.

Alignment of SEQ ID No 10 with SEQ ID No 8:
showed 99% sequence identity between nucleotides 1293 to 2658 of SEQ ID 10 and nucleotides 1 to 1366 of SEQ ID No 8 (1361 of 1366 matching bases), and
100% sequence identity between nucleotides 3222 to 3526 of SEQ ID 10 and nucleotides 1367 to 1671 of SEQ ID No 8; and
identified a putative intron sequence between nucleotides 2659 and 3221 of SEQ ID 10.

Example 3

Isolation and Characterization of a Pollen-Preferential Promoter Region ("$P_{OsPOL}$") Corresponding to the Rice Pollen-Preferential Genes of Example 2

Primer TSOL109 (SEQ ID No 5) was designed based on the recognition sites of restriction enzymes BgIII and EcoRV and nucleotides 320 to 336 of SEQ ID No 4 (approximately 1110 bp upstream of the putative translation initiation codon). Primer TSOL119 (SEQ ID No 6) was designed based on the recognition sites of restriction enzyme NcoI and nucleotides 1412 to 1430 of SEQ ID No 4 (upstream of the putative translation initiation codon). Primers TSOL 109 and TSOL 119 were used in a polymerase chain reaction (PCR) on genomic DNA of *Oryza sativa* japonica Lemont.

Each PCR reaction contained Advantage-GC cDNA Polymerase Mix (BD Biosciences), 10 pmol TSOL109 primer, 10 pmol TSOL 119 primer and 200 ng genomic DNA in a total volume of 50 µl overlaid with mineral oil.

PCR cycles were as follows:
1 PCR cycle included a denaturation temperature of 95° C. for 3 min
31 PCR cycles included a denaturation temperature of 94° C. for 45 sec, a primer annealing temperature of 55° C. for 45 sec and an extension temperature of 72° C. for 1 min 30 sec.
1 PCR cycle included an extension temperature of 72° C. for 5 min A 1137 bp DNA fragment was purified from agarose with a gel extraction kit (Qiagen) and cloned into pGEM-T Easy®, resulting in plasmid pTS320. The DNA sequence of the PCR fragment was obtained by the dideoxy chain termination method. The complete nucleotide sequence of the PCR fragment is represented in SEQ ID No 7.

Alignment of SEQ ID No 7 with SEQ ID No 4:
showed 99% sequence identity between nucleotides 16 to 1127 of SEQ ID No 7 and nucleotides 320 to 1431 of SEQ ID No 4 (1108 of 1112 matching bases), and
identified two putative transcription start sites at nucleotide positions 932 and 940 of SEQ ID No 7.

Alignment of SEQ ID No 7 with SEQ ID No 10, showed 96% sequence identity between nucleotides 231 to 955 of SEQ ID No 7 and nucleotides 444 to 1170 of SEQ ID No 10 (708 of 730 matching bases).

Example 4

Construction of a Plant Transformation Vector Comprising a Pollen Lethality DNA Under the Control of Pollen-Preferential Promoter $P_{OsPOL}$ (of Example 3) and a Co-Regulating Gene A 1122 bp BgIII-NcoI fragment of pTS320 (EXAMPLE 3) was ligated to a 3690 bp BgIII-NcoI fragment of plasmid pTS207, yielding plasmid pTS321.

Plasmid pTS207 is a plasmid derived from plasmid pUC18 (Yanisch-Perron et al. (1985) *Gene* 33:103) and contains a DNA sequence encoding barnase (Hartley (1988) *J Mol Biol* 202:913) under the control of the Zm13 promoter (WO 93/25695) from *Zea mays*.

A 1249 bp EcoRV-AatII fragment of pTS321 was ligated to a 12857 bp EcoRV-AatII fragment of pTTS45, yielding plasmid pTTS49 (FIG. 1).

Plasmid pTTS45 is a plasmid that contains a pollen-lethality gene (as described in WO 93/25695), a coregulating gene (as described in WO 96/26283) and a marker gene:

The pollen-lethality gene comprises the coding sequence of the barnase gene from *Bacillus amyloliquifaciens* ["barnase"; Hartley (1988) *J Mol Biol* 202: 913] as the pollen-lethality DNA, the Zm13 promoter (WO 93/25695; supra) from *Zea mays* as the pollen-specific promoter and 3' untranslated region of the nopaline synthase gene from *Agrobacterium tumefaciens* [Depicker et al. (1982) *Journal of Molecular and Applied Genetics* 1: 561-573];

The correlating gene comprises the coding sequence of an improved barstar as described in WO98/10081 under the control of the promoter region of the 35S transcript of CaMV ["35S promoter"; Odell et al. (1985) *Nature* 313: 810-812] and the 3' untranslated region of gene 7 from *Agrobacterium tumefaciens* [Dhaese et al., (1983) *The EMBO J* 2: 419];

The marker gene comprises the coding sequence of the bialaphos resistance gene from *Streptomyces hygroscopicus* ["bar"; Thompson et al. (1987) *The EMBO J* 6: 2519-2523] under the control of the promoter region of the gos2 gene from rice ["gos2 promoter"; de Pater et al. (1992) *The Plant J* 2: 837] and 3' untranslated region of the nopaline synthase gene from *Agrobacterium tumefaciens* [Depicker et al. (1982), supra]. The bar gene provides resistance to phosphinothricin (PPT) and Liberty® herbicide.

Example 5

Transformation of Rice with Plant Transformation Vector pTTS49 Comprising a Pollen-Lethality DNA (Barnase) Under the Control of Pollen-Preferential Promoter Region $P_{OsPOL}$ and a Coregulating Gene (35S Promoter-Barstar) Linked to a Marker Gene (Gos2 Promoter-Bar) (of Example 4)

Immature embryos of *Oryza sativa* japonica were transformed with *Agrobacterium* strain Ach5 C3 containing Ti plasmid pGV4000 and transformation vector pTTS49. Selection was done on phosphinothricin (PPT) at all stages except plantlet regeneration, which was done in the absence of PPT to accelerate growth. This resulted in a set of primary transformants (plants of generation $T_0$).

Alternatively, transformation of rice plants can be performed by direct gene transfer. For example, bombardment of immature embryos with gold particles, carrying appropriate plasmid DNA, and regeneration of transformed plants from the embryos by the procedures described by Christou et al., (1991) *Bio/Technology* 9:957. Alternatively, protoplasts can be transformed using the procedures described by Datta et al. (1992) *Plant Mol Biol* 20:619-629, followed by regeneration of transformed plants from the protoplasts.

Example 6

Analysis of Primary Transformants (T$_0$ Plants) of Rice Comprising a Pollen-Lethality DNA (Barnase) Under the Control of Pollen-Preferential Promoter Region P$_{OsPOL}$ and a Coregulating Gene (35S Promoter-Barstar) linked to a marker gene (gos2 promoter-bar) (of Example 5)

The expression of the pollen-lethality gene and the coregulating gene were determined by cytological examination of the anther and by morphological examination of the plants (plant quality, color, height, number of tillers). In this regard, plants expressing both the pollen-lethality and coregulating genes were expected to be normal except for their pollen: as the expression of the pollen-lethality gene results in sterile pollen, about 50% of the pollen a plant containing the pollen-lethality gene will be sterile.

The degree of male sterility of the plants was assessed by analyzing the percentage pollen fertility. The percentage pollen fertility was observed after staining pollen grains with Iodine Potassium Iodide (IKI) solution (2% KI, 0.2% I$_2$). Samples for pollen were collected from at least three spikelets from individual plants. Anthers were collected in eppendorf tubes containing IKI solution. After staining for at least 5 min, the pollen was put on a glass slide. At least two microscopic slides were used to count sterile pollen grains (i.e., unstained) and fertile pollen grains (stained); the percentage pollen fertility was computed as follows:

$$\frac{\text{Total number of pollen grains} - \text{Number of sterile pollen grains}}{\text{Total number of pollen grains}_i} \times 100$$

TABLE II

Percentage pollen fertility of primary transformants obtained in Example 5

| Name T$_o$ Plant | Pollen fertility (%) |
|---|---|
| Control 1.1 | 90-99 |
| Control 1.2 | 90 |
| Plant 1.1.1 | 10-30 |
| Plant 1.1.2 | 10-30 |
| Plant 1.1.3 | 10-15 |
| Plant 1.4.1 | 50 |
| Plant 1.4.2 | 50-70 |
| Plant 1.6.2 | 50-70 |
| Plant 1.7.1 | 70 |
| Plant 1.7.2 | 80 |
| Plant 1.7.3 | 50 |
| Plant 1.8.1 | 20 |
| Plant 1.8.2 | 40-50 |
| Plant 1.9.2 | 20 |
| Plant 1.9.3 | 50 |
| Plant 1.10.1 | 5 |
| Plant 1.10.2 | 1 |
| Plant 1.10.3 | 1 |
| Plant 1.11.1 | 60 |
| Plant 1.13.1 | 50 |
| Plant 1.13.2 | 50 |
| Plant 1.15.1 | 10 |
| Plant 1.15.3 | 10 |
| Control 2.1 | 90-95 |
| Control 2.2 | 95-100 |
| Plant 2.1.1 | 60 |
| Plant 2.1.3 | 70 |
| Plant 2.2.2 | 50-60 |
| Plant 2.3.1 | 50 |

TABLE II-continued

Percentage pollen fertility of primary transformants obtained in Example 5

| Name T$_o$ Plant | Pollen fertility (%) |
|---|---|
| Plant 2.4.1 | 20-30 |
| Plant 2.4.2 | 50 |
| Plant 2.4.3 | 10 |
| Plant 2.6.1 | 50-60 |
| Plant 2.6.2 | 60-70 |
| Plant 2.6.3 | 50 |
| Plant 2.7.1 | 5 |
| Plant 2.7.2 | 30-40 |
| Plant 2.7.3 | 30-40 |
| Plant 2.8.1 | 50 |
| Plant 2.8.3 | 70 |
| Plant 2.9.2 | 40 |
| Plant 2.9.3 | 50 |
| Plant 2.10.2 | 50 |
| Plant 2.11.3 | 80 |
| Plant 2.12.1 | 50 |
| Plant 2.12.2 | 5 |
| Plant 2.13.2 | 50 |
| Plant 2.14.3 | 50 |
| Plant 2.15.1 | 5 |
| Plant 2.15.2 | 30-40 |
| Plant 2.16.3 | 50 |
| Plant 2.17.1 | 60 |
| Plant 2.17.2 | 50 |
| Plant 2.18.3 | 50 |
| Plant 2.19.2 | 50 |
| Plant 2.20.1 | 50-60 |
| Plant 2.21.1 | 70-80 |
| Plant 2.21.2 | 50 |
| Plant 2.23.1 | 50 |
| Plant 2.24.1 | 50-60 |
| Plant 2.25.1 | 60 |

The viability of pollen can also be determined by analyzing the staining of isolated pollen as described by Alexander (1969) *Stain Technology* 44:117. Alternatively, isolated pollen can be incubated for 30 minutes at 24° C. in the following reaction mixture: 100 mM phosphate buffer pH 7.8, 100 mM Sodiumsuccinate and 1 mM Nitro Blue Tetrazolium, followed by visual inspection of formazan precipitation in viable pollen. The viability of microspores can also be determined as described for example by Heslop-Harrison and Heslop-Harrison (1970) *Stain Technology* 45:115 or by embedding flower buds in plastic at different developmental stages and subjecting the buds to histochemical staining with the succinate dehydrogenase assay, both as described by De Block and Debrouwer (1992) *The Plant J* 2:261.

The integration of the pollen-lethality gene and the coregulating gene was analyzed by means of Southern hybridization.

Genomic DNA was prepared from plant tissue according to the protocol described by Dellaporta et al. (1983) *Plant Mol Biol Reporter* 1:19, supplemented by a treatment with RNase to remove remaining RNA. A nontransformed plant was used as a control. Samples of the DNA were digested with appropriate restriction enzymes and subjected to horizontal agarose electrophoresis. Southern transfer to Hybond N+ (Amersham International PLC, Amersham, United Kingdom) membranes by means of alkali blotting of DNA and subsequent hybridization were performed as recommended by the manufacturer (Amersham Hybond-N+ leaflet). Suitable radioactive probes were prepared with the multi-prime DNA labeling kit (Amersham) according to the protocol supplied by the manufacturer, which is derived from published procedures (Feinberg and Vogelstein (1983) *Anal Biochem* 132:6). The banding patterns showed that at least the pollen-lethality gene was integrated into the plant genomic DNA.

Alternatively, the presence of the pollen-lethality gene or the coregulating gene can be analyzed by means of polymerase chain reaction (PCR) analysis: DNA is prepared according to the protocol described by Dellaporta et al. supra. Representative fragments of the pollen-lethality gene or the coregulating gene are amplified using appropriate oligonucleotide probes.

Example 7

Analysis of $T_1$ Progeny Plants Obtained by Selfing $T_0$ Rice Plants Comprising a Pollen-Lethality DNA (Barnase) Under the Control of Pollen-Preferential Promoter Region $P_{OsPOL}$ and a Coregulating Gene (35S Promoter-Barstar) Linked to a Marker Gene (Gos2 Promoter-Bar) (of Examples 5 and 6)

$T_1$ progeny plants of five selected (single copy) $T_0$ plants (Example 5 and 6) were analyzed as follows:
the $T_0$ plants were selfed
$T_1$ seeds were harvested
the seeds were soaked in 0.5% Behlate® fungicide (DuPont) and 0.4% AmistaR® fungicide (Syngenta) for 1' hour and placed on a wetted filter paper for 6 days
the seeds were sown in trays
the emergence was scored
the $T_1$ plants were sprayed with 0.4% Liberty® herbicide (Bayer)
the segregation was scored upon Liberty® spray:
About 50% of the $T_1$ progeny plants obtained from selfing the $T_0$ plants containing one copy of the pollen-lethality gene and the co-regulating gene coupled to the marker gene, were. Liberty®-resistant (Table III).

TABLE III

Number of Liberty ®-resistant $T_1$ progeny plants on total number of $T_1$ plants analyzed obtained by selfing $T_0$ rice plants comprising a pollen-lethality DNA (barnase) under the control of pollen-preferential promoter region $P_{OsPOL}$ and a coregulating gene (35S promoter-barstar) linked to a marker gene (gos2 promoter-bar)

| Name selfed $T_o$ plant | Number of resistant/total number of $T_1$ progeny plants analyzed | % Resistant $T_1$ progeny plants |
| --- | --- | --- |
| Plant 1.13.1 | 23/48 | 48 |
| Plant 2.6.1. | 16/44 | 36 |
| Plant 2.9.1 | 23/47 | 49 |
| Plant 2.17.1 | 34/55 | 62 |
| Plant 2.25.1 | 24/53 | 45 |

Example 8

Analysis of $F_1$ Progeny Plants Obtained by Crossing Liberty®-Resistant $T_1$ Rice Plants Comprising a Pollen-Lethality DNA (Barnase) Under the Control of Pollen-Preferential Promoter Region $P_{OsPOL}$ and a Coregulating Gene (35S Promoter-Barstar) Linked to a Marker Gene (Gos2 Promoter-Bar) (of Examples 5, 6 and 7) with Plants not Comprising Said Genes as Male or Female Parent $T_1$, seeds were harvested from $T_0$ rice plants comprising a pollen-lethality DNA (barnase) under the control of pollen-preferential promoter region $P_{OsPOL}$ and a coregulating gene 35 promoter-barstar) linked to a marker gene (gos2 promoter-bar), soaked in 0.5% Benlate® fungicide (DuPont) and 0.4% Amistar® fungicide (Syngenta) for 1 hour, placed on a wetted filter paper for 6 days, and sown in trays
the $T_1$, plants were sprayed with 0.4% Liberty® herbicide (Bayer) and Liberty® resistant $T_1$ plants were transferred to the field and crossed with plants that do not contain the pollen-lethality gene ($P_{OsPOL}$-barnase), the coregulating gene (35S promoter-barstar) or the marker gene (gos2 promoter-bar)
$F_1$ seeds were harvested, soaked in 0.5% Benlate® fungicide (DuPont) and 0.4% Amistar® fungicide (Syngenta) for 1 hour, placed on a wetted filter paper for 6 days, and sown in trays
the $F_1$ plants were sprayed with 0.4% Liberty® herbicide (Bayer) and the segregation was scored upon Liberty® spray:
None of the $F_1$ progeny plants obtained from a cross between the Liberty®-resistant $T_1$, plants comprising the pollen-lethality ($P_{OsPOL}$-barnase) and coregulating genes (35S promoter-barstar) linked to the marker gene (gos2 promoter-bar) as male parent and male-sterile rice plants M-201 NP GENETIC MS (Accession number PI 543853; USDA, ARS, National Genetic Resources Program. *Germplasm Resources Information Network—(GRIN)*) as female parent were Liberty®-resistant (Table IV)

TABLE IV

Number of Liberty ®-resistant $F_1$ progeny plants on total number of $F_1$ plants analyzed obtained by crossing Liberty ®-resistant $T_1$ plants comprising a pollen-lethality DNA (barnase) under the control of pollen-preferential promoter region $P_{OsPOL}$ and a coregulating gene (35S promoter-barstar) linked to a marker gene (gos2 promoter-bar) as male parent with male-sterile plants not comprising the pollen-lethality ($P_{OsPOL}$-barnase) and coregulating genes (35S promoter-barstar) linked to the marker gene (gos2 promoter-bar) as female parent

| Liberty ®-resistant $T_1$ plants used in cross derived from $T_0$ plant: | Number of resistant/total number of $F_1$ progeny plants analysed |
| --- | --- |
| Plant 1.13.1 | 0/46 |
| Plant 2.6.1. | 0/48 |
| Plant 2.9.1 | 0/49 |
| Plant 2.17.1 | 0/49 |
| Plant 2.25.1 | 0/49 | about 50% of the F1 progeny plants obtained from a cross between the Liberty®-resistant $T_1$ plants comprising the pollen-lethality ($P_{OsPOL}$-barnase) and coregulating genes (35S promoter-barster)linked to the marker gene (gos2 promoter-bar) as female parent and plants not comprising the pollen-lethality ($P_{OsPOL}$-barnase) and coreulating genes (35S promoter-barster) linked to the marker gene (gos2 promoter-bar) as male parent as Liberty®-resistant The presence and the expression of the pollen-lethality gene, the coregulating gene and the marker gene can be analyzed as described in Example 5, 6 and 7.

Example 9

Construction of Plant Transformation Vectors Comprising Chimeric Genes Encoding dsRNA Capable of Reducing the Expression of the Pollen-Preferential Genes of Example 2 and Introduction in Plants Using standard cloning techniques the following chimeric genes encoding dsRNA capable of reducing the expression of the pollen-preferential genes of Example 2 are constructed and introduced into T-DNA vectors, together with an appropriate selective marker gene:

1) A dsRNA encoding chimeric gene (P35S-dsRNA/OsPOL) comprising the following operably linked DNA fragments:
   P35S: Promoter region from the Cauliflower Mosaic Virus 35S (Odell et al., (1985) Nature 313: 810-812)
   OsPOL$^{sense}$. An about 200 bp fragment from the promoter and/or the transcribed DNA region of the pollen-preferential genes comprised in SEQ ID No 4 or SEQ ID No 10, or from SEQ ID No 8, encoding a pollen-preferential protein. This fragment is cloned in sense orientation.
   Pdk-intron: Sequence of the second intron from the pyruvate orthophosphate dikinase gene (termed pdk gene) from *Flaveria trinervia* (Rosche & Westhoff (1995) Plant Molecular Biology 29: 663-678)
   OsPOL$^{antisense}$: The about 200 bp OsPOL$^{sense}$ fragment cloned in antisense orientation.
   3'ocs: the 3' untranslated end from the octopine synthase gene (De Greve et al. (1982) J Mol Appl Genet 1: 499-512; Gielen et al. (1984) EMBO J 3: 835-846).
2) A dsRNA encoding chimeric gene (Pnos-dsRNA/OsPOL), similar to the chimeric gene of point 1, wherein the CaMV35S promoter has been exchanged for a nopaline synthase promoter from *Agrobacterium tumefaciens*, through standard cloning techniques
3) A dsRNA encoding chimeric gene (POsPOL-dsRNA/Os-POL), similar to the chimeric gene of point 1, wherein the CaMV35S promoter has been exchanged for a rice pollen-preferential promoter according to this invention, through standard cloning techniques The above T-DNA vectors' are introduced into *Agrobacterium* strain Ach5 C3 containing Ti plasmid pGV4000. The resulting *Agrobacterium* strains are used to transform rice plants as described in Example 5.

Example 10

Analysis of the Transgenic Rice Plants of Example 9 and Progeny Plants Thereof The expression of the chimeric genes of Example 9 and the effect thereof on the expression of the pollen-preferential genes of Example 2 and on the phenotype of the transgenic rice plants and progeny thereof is determined essentially as described in Examples 6, 7, and 8:

The presence of the chimeric genes in the transgenic rice plants of Example 9 and progeny thereof is analyzed by means of PCR as described in Example 6.

The integration of the chimeric genes in the transgenic rice plants of Example 9 and progeny thereof is analyzed by means of Southern hybridization as described in Example 6.

The effect of the expression of the chimeric genes of Example 9 on the expression of the pollen-preferential genes of Example 2 in the transgenic rice plants of Example 9 and progeny thereof, is analyzed by comparing the expression of the pollen-preferential genes of Example 2 in rice plants containing the chimeric genes, of Example 9 and rice plants not containing the chimeric genes of Example 9 through northern blot analysis as described in Example 1.

The phenotype of the transgenic rice plants of Example 9 and progeny thereof is analyzed
   by cytological examination of the anther, such as analysis of the degree of pollen fertility as described in Example 6.
   by morphological examination of the plants, such as plant quality, color, height, number of tillers, and the like.

Needless to say, the use of the rice pollen-preferential promoters and promoter regions of this invention is not limited to the transformation of any specific plant(s). They can be useful in any plant where they are capable of controlling gene expression, and where such expression is to occur preferentially in microspores and/or pollen of the plant.

Also, the use of these promoters is not limited to the control of pollen-lethality DNA but can be used to control the expression of any gene preferentially in microspores and/or pollen.

Furthermore, this invention is not limited to the specific pollen-preferential promoters and promoter regions described in the foregoing Examples. Rather, this invention encompasses promoters and promoter regions equivalent to those of Example 2 and 3 that can be used to control the expression of a structural gene, such as a pollen-lethality DNA, preferentially in microspores and/or pollen of a plant. Indeed, it is believed that the DNA sequence of the promoter regions of Example 2 and 3 can be modified by replacing some of their nucleotides with other nucleotides, provided that such modifications do not alter substantially the ability of polymerase complexes, including transcription activators, of microspores and/or pollen cells, to recognize the promoter, as modified.

Thus, in summary, the instant specification describes a rice pollen-preferential promoter region comprising the nucleotide sequence of SEQ ID No 7 from the nucleotide at position 16 to the nucleotide at position 1126, or parts thereof having promoter activity.

The invention claimed is:

1. A pollen-preferential chimeric gene comprising the following operably linked DNA fragments:
   a) an isolated pollen-preferential promoter region comprising
      i. the nucleotide sequence of SEQ ID No 7 from the nucleotide at position 16 to the nucleotide at position 1126;
      ii. the nucleotide sequence of SEQ ID No 7 from the nucleotide at position 16 to the nucleotide at position 940; or
      iii. the nucleotide sequence of SEQ ID No 7 from the nucleotide at position 16 to the nucleotide at position 932; and
   b) a heterologous DNA region encoding an antisense RNA, a sense RNA, or a double-stranded RNA, which when produced in a plant cell, inhibits or reduces the expression of a target gene of interest in said plant cell, compared to the expression of said gene in a plant cell not comprising said DNA region, wherein said target gene is an endogenous plant gene, the product of which is essential for the normal development of microspores and/or pollen.

2. A pollen-preferential chimeric gene comprising the following operably linked DNA fragments:
   a) an isolated pollen-preferential promoter region comprising
      i the nucleotide sequence of SEQ ID No 7 from the nucleotide at position 16 to the nucleotide at position 1126;
      ii. the nucleotide sequence of SEQ ID No 7 from the nucleotide at position 16 to the nucleotide at position 940; or
      iii. the nucleotide sequence of SEQ ID No 7 from the nucleotide at position 16 to the nucleotide at position 932; and
   b) a heterologous DNA region encoding a ribozyme, which when produced in a plant cell, specifically cleaves a target gene sequence in said plant cell, wherein said target gene sequence is a sequence from an endogenous plant gene, the product of which is essential for the normal development of microspores and/or pollen.

3. A plant transformation vector comprising:
   a) a pollen-preferential chimeric gene comprising the following operably linked DNA fragments:
      i. an isolated pollen-preferential promoter region comprising
         a. the nucleotide sequence of SEQ ID No 7 from the nucleotide at position 16 to the nucleotide at position 1126;
         b. the nucleotide sequence of SEQ ID No 7 from the nucleotide at position 16 to the nucleotide at position 940; or
         c. the nucleotide sequence of SEQ ID No 7 from the nucleotide at position 16 to the nucleotide at position 932; and
      ii. a heterologous DNA region encoding a biologically active RNA, protein, or polypeptide; and
   b) a second chimeric gene comprising
      i. a second heterologous DNA region encoding a biologically active RNA, protein or polypeptide, which when produced together with the gene product of said pollen-preferential chimeric gene, counteracts, prevents or inhibits the activity of said gene product; and
      ii. a plant expressible promoter, which directs expression of said second heterologous DNA region at least in cells other than microspore and/or pollen cells.

4. A plant cell, plant tissue, plant, plant seed, at plant grain, comprising:
   a) a pollen-preferential chimeric gene comprising the following operably linked DNA fragments:
      i. an isolated pollen-preferential promoter region comprising
         a. the nucleotide sequence of SEQ ID No 7 from the nucleotide at position 16 to the nucleotide at position 1126;
         b. the nucleotide sequence of SEQ ID No 7 from the nucleotide at position 16 to the nucleotide at position 940; or
         c. the nucleotide sequence of SEQ ID No 7 from the nucleotide at position 16 to the nucleotide at position 932; and
      ii. a heterologous DNA region encoding a biologically active RNA, protein, or polypeptide: and
   b) a second chimeric gene comprising
      i. a second heterologous DNA region encoding a biologically active RNA, protein or polypeptide, which when produced together with the gene product of said pollen-preferential, chimeric gene, counteracts, prevents or inhibits the activity of said gene product; and
      ii. a plant expressible promoter, which directs expression of said second heterologous DNA region at least in cells other than microspore and/or pollen cells.

5. The plant cell, plant tissue, plant, plant seed, or plant grain of claim 4, wherein said heterologous DNA region from said pollen-preferential chimeric gene encodes barnase, and wherein said second heterologous DNA region encodes barstar.

6. The plant cell, plant tissue, plant, plant seed, or plant grain of claim 4 or 5, wherein said plant expressible promoter, which directs expression of said second heterologous DNA region, is a CaMV35S promoter.

7. The plant cell, plant tissue, plant, or plant seed of claim 4, which is a monocotyledonous plant cell, plant tissue, plant, or plant seed.

8. The plant cell, plant tissue, plant, plant seed, or plant grain of claim 4, which is a cereal plant cell, plant tissue, plant, or plant seed.

9. The plant cell, plant tissue, plant, plant seed, or plant grain of claim 4, which is a rice, corn, or wheat plant cell, plant tissue, plant, or plant seed.

10. A method for expressing an antisense RNA, a sense RNA, or a double-stranded RNA preferentially in microspore and/or pollen cells of a plant, wherein said RNA, when produced in a plant cell, inhibits or reduces the expression of a target gene of interest in said plant cell, compared to the expression of said gene in a plant cell not comprising said DNA region, wherein said target gene is an endogenous plant gene, the product of which is essential for the normal development of microspores and/or pollen, comprising the steps of:
   I) providing a plant with the pollen-preferential chimeric gene of claim 1; and
   II) growing said plant.

11. A pollen-preferential chimeric gene comprising the following operably linked DNA fragments;
   c) an isolated pollen-preferential promoter region comprising
      i. the nucleotide sequence of SEQ ID No 7 from the nucleotide at position 16 to the nucleotide at position 1126;
      ii. the nucleotide sequence of SEQ ID No 7 from the nucleotide at position 16 to the nucleotide at position 940; or
      iii. the nucleotide sequence of SEQ ID No 7 from the nucleotide at position 16 to the nucleotide at position 932; and
   d) a heterologous DNA region encoding a barnase.

12. A method for expressing a ribozyme preferentially in microspore and/or pollen cells of a plant, wherein said ribosome when produced in a plant cell, specifically cleaves a target gene sequence in said plant cell, wherein said target gene sequence is a sequence from an endogenous plant gene, the product of which is essential for the normal development of microspores and/or pollen, comprising:
   I) providing a plant with the pollen-preferential chimeric gene of claim 2; and
   II) growing said plant.

13. A method for expressing a barnase preferentially in microspore and/or pollen cells of a plant, comprising:
  I) providing a plant with the pollen-preferential chimeric gene of claim 11, and
  II) growing said plant.

14. The method of claim 10, 12 or 13, wherein said plant is provided with said pollen-preferential chimeric gene by transforming a cell of a plant with said chimeric gene and by regenerating said plant from said transformed cell.

15. The method of claim 14, wherein said plant cell is transformed with the plant transformation vector of claim 3.

16. The method of claim 10, 12 or 13, which further comprises the step of providing said plant with a second chimeric gene comprising
  a) a second heterologous DNA region encoding a biologically active RNA, protein or polypeptide, which when produced together with the gene product of said pollen-preferential chimeric gene, counteracts, prevents or inhibits the activity of said gene product; and
  b) a plant expressible promoter, which directs expression of said second heterologous DNA region at least in cells other than microspore and/or pollen cells.

17. The method of claim 16, wherein said plant is provided with said second chimeric gene by transforming a cell of a plant with said second chimeric gene and by regenerating said plant from said transformed cell.

18. The method of claim 17, wherein the plant cell is transformed with the plant transformation vector of claim 3.

19. A method for disturbing the metabolism, functioning and/or development of a microspore and/or pollen cell, which comprises the steps of:
  I) providing a plant with the pollen-preferential chimeric gene of claim 1, 2, or 11; and
  II) growing said plant.

20. The method of claim 19, which further comprises the step of providing said plant with a second chimeric gene comprising
  a) a second heterologous DNA region encoding a biologically active RNA, protein or polypeptide, which when produced together with the gene product of said pollen-preferential chimeric gene, counteracts, prevents or inhibits the activity of said gene product; and
  b) a plant expressible promoter, which directs expression of said second heterologous DNA region at least in cells other than microspore and/or pollen cells.

21. A method for inhibiting or reducing the expression of a target gene of interest in a microspore and/or pollen cell, which comprises the steps of:
  I) providing a plant with the pollen-preferential chimeric gene of claim 1, 2 or 11; and
  II) growing said plant.

22. The method of claim 21, which further comprises the step of providing said plant with a second chimeric gene comprising
  a) a second heterologous DNA region encoding a biologically active RNA, protein or polypeptide, which when produced together with the gene product of said pollen-preferential chimeric gene, counteracts, prevents or inhibits the activity of said gene product; and
  b) a plant expressible promoter, which directs expression of said second heterologous DNA region at least in cells other than microspore and/or pollen cells.

23. A method for producing a plant with modified pollen-fertility properties, which comprises the steps of:
  I) providing a plant with the pollen-preferential chimeric gene of claim 1, 2 or 11; and
  II) growing said plant.

24. The method of claim 23, which further comprises the step of providing said plant with a second chimeric gene comprising
  a) a second heterologous DNA region encoding a biologically active RNA, protein or polypeptide, which when produced together with the gene product of said pollen-preferential chimeric gene, counteracts, prevents or inhibits the activity of said gene product; and
  b) a plant expressible promoter, which directs expression of said second heterologous DNA region at least in cells other than microspore and/or pollen cells.

* * * * *

UNITED STATES PATENT AND TRADEMARK OFFICE
CERTIFICATE OF CORRECTION

PATENT NO. : 7,667,097 B2
APPLICATION NO. : 11/578428
DATED : February 23, 2010
INVENTOR(S) : Scheirlinck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

Signed and Sealed this

Seventh Day of December, 2010

David J. Kappos
*Director of the United States Patent and Trademark Office*